United States Patent
Sasagawa

(10) Patent No.: US 10,859,449 B2
(45) Date of Patent: Dec. 8, 2020

(54) DISTRIBUTION MEASURING SENSOR, DISTRIBUTION MEASURING SENSOR SYSTEM, DISTRIBUTION MEASURING PROGRAM, AND RECORDING MEDIUM

(71) Applicant: HIROSAKI UNIVERSITY, Hirosaki (JP)

(72) Inventor: Kazuhiko Sasagawa, Aomori (JP)

(73) Assignee: HIROSAKI UNIVERSITY, Aomori (JP)

(*) Notice: Subject to any disclaimer, the term of this patent is extended or adjusted under 35 U.S.C. 154(b) by 30 days.

(21) Appl. No.: 16/347,130

(22) PCT Filed: Nov. 6, 2017

(86) PCT No.: PCT/JP2017/039936
§ 371 (c)(1),
(2) Date: May 2, 2019

(87) PCT Pub. No.: WO2018/084284
PCT Pub. Date: May 11, 2018

(65) Prior Publication Data
US 2020/0072686 A1    Mar. 5, 2020

(30) Foreign Application Priority Data
Nov. 4, 2016    (JP) .................................. 2016-216304

(51) Int. Cl.
*G01L 1/20*    (2006.01)
*A61B 5/103*    (2006.01)
(Continued)

(52) U.S. Cl.
CPC .............. *G01L 1/205* (2013.01); *A61B 5/103* (2013.01); *G01L 5/16* (2013.01); *A61B 2562/0247* (2013.01); *A61B 2562/046* (2013.01)

(58) Field of Classification Search
CPC .............. G01L 1/205; G01L 1/25; G01L 5/16
See application file for complete search history.

(56) References Cited

U.S. PATENT DOCUMENTS 4,951,510 A * 8/1990 Holm-Kennedy ........................... G01P 15/0802
73/510
5,571,973 A    11/1996 Taylot
(Continued)

FOREIGN PATENT DOCUMENTS

JP    3983638 B2    9/2007
JP    2012-058159 A    3/2012
(Continued)

OTHER PUBLICATIONS

International Preliminary Report on Patentability dated May 16, 2019 in corresponding International Application No. PCT/JP2017/039936.
(Continued)

*Primary Examiner* — Jewel V Dowtin
(74) *Attorney, Agent, or Firm* — Miles & Stockbridge, P.C.

(57) ABSTRACT

To provide a distribution measuring sensor system and the like having a high spatial resolution and can greatly reduce a wiring region even if many sensor units for the measurement of a contact pressure and a shear stress acting on an interface between a living body and an object are integrated. A distribution measuring sensor 10 has a configuration in which sensor units Uij which measure a shear stress in a direction of a plane and a contact pressure in a direction perpendicular to the plane are arranged at each element of a matrix M. The sensor units Uij are constituted of an upper electrode UijH common to measurement of the shear stress and the contact pressure, and a lower electrode UijL arranged below the upper electrode UijH through a pressure
(Continued)

sensitive material 20. Each sensor unit Uij in the x axis direction arranged in the same column j of the matrix M has each upper electrode UijH connected in the column j direction in common through the connecting line Cj. Each sensor unit Uij in the y axis direction arranged in the same row i of the matrix M has each lower electrode UijL connected in the row i direction in common through the connecting line Ri.

11 Claims, 23 Drawing Sheets

(51) Int. Cl.
    *G01N 3/24*      (2006.01)
    *G01L 5/16*      (2020.01)

(56) References Cited

U.S. PATENT DOCUMENTS

| | | |
|---|---|---|
| 7,174,793 B2 | 2/2007 | Morimoto |
| 7,343,813 B1 | 3/2008 | Harrington |
| 7,861,605 B2 * | 1/2011 | Ogawa ............... G01L 5/164 |
| | | 73/862.69 |
| 9,250,143 B2 * | 2/2016 | Harrington ............ G01L 1/142 |
| 9,347,838 B2 * | 5/2016 | Chen .................... B25J 13/083 |
| 9,459,736 B2 * | 10/2016 | Badaye ................ G06F 3/0416 |
| 9,823,141 B2 * | 11/2017 | Li ........................ G01L 1/146 |
| 2005/0005703 A1 * | 1/2005 | Saito ..................... G06F 3/044 |
| | | 73/780 |
| 2017/0115171 A1 | 4/2017 | Huang et al. |

FOREIGN PATENT DOCUMENTS

| | | |
|---|---|---|
| JP | 2012168064 A | 9/2012 |
| JP | 2015169532 A | 9/2015 |
| WO | 2015176032 A1 | 11/2015 |

OTHER PUBLICATIONS

International Search Report of PCT/JP2017/039936, dated Nov. 28, 2017.

* cited by examiner (A)

(B)

Applied shear stress $\tau$ x (Applied shear stress) [kPa]

(A)

(B)

(A)

(B)

DISTRIBUTION MEASURING SENSOR, DISTRIBUTION MEASURING SENSOR SYSTEM, DISTRIBUTION MEASURING PROGRAM, AND RECORDING MEDIUM

TECHNICAL FIELD

The present invention relates to a distribution measuring sensor which can simultaneously measure a shear stress in each axis (an x axis, a y axis) direction of a plane and a contact pressure in an axis (a z axis) direction perpendicular to the plane, a distribution measuring sensor system using the distribution measuring sensor, a distribution measuring program, and the like.

BACKGROUND ART

Measurement of a contact pressure and a shear stress produced on a solid interface, especially an interface between a living body and an object has been highly demanded in various fields such as sports engineering or medical science. However, a sensor used for such measurement is thick and hard, and hence there is a problem that direct measurement of a contact pressure and a shear stress produced on the interface between the living body and the object cannot be performed.

To solve the problem, a thin flexible sensor device which uses a conductive polymer material such as a polypyrrole thin film for a stress sensitive element and measures a contact pressure and a shear stress has been recently developed (see Patent Reference 1).

PRIOR ART LIST

Patent Reference

Patent Reference 1: Japanese Patent Publication No. 5688792

SUMMARY OF THE INVENTION

Problem to be Solved by the Invention

However, since the sensor device is configured to solely function, many sensor devices must be integrated to grasp a distribution of a tactile sense. At the integration, a wiring region connecting many sensor devices increases, a design becomes complicated, and there is also a problem of an increase in manufacturing costs. Thus, a sensor which has a high spatial resolution applicable to the interface between the living body and the object is yet to be realized.

Therefore, it is an object of the present invention to solve the above-described problem and to provide a distribution measuring sensor system or the like with a high spatial resolution which has characteristics of a thin flexible sensor device applicable to measurement of a contact pressure and a shear stress acting on an interface between a living body and an object, can greatly reduce a wiring region even if many sensor devices are integrated to grasp a distribution of a tactile sense, simplify a design, and suppress an increase in manufacturing costs.

Means for Solving Problem

A distribution measuring sensor of the present invention is a distribution measuring sensor having a configuration in which sensor units which measure a shear stress in each axis (an x axis, a y axis) direction of a plane and a contact pressure in an axis (a z axis) direction perpendicular to the plane are arranged in a matrix form, wherein the sensor unit comprises: an upper electrode which is used for measurement of the shear stress and the contact pressure in common and a lower electrode which is arranged through the upper electrode and a pressure sensitive material and is constituted of electrodes individually used for measurement of the shear stress and that of the contact pressure; an x axis shear stress measuring unit which measures the shear stress in the x axis direction acting between the upper electrode and the lower electrode; a y axis shear stress measuring unit which measures the shear stress in the y axis direction acting between the upper electrode and the lower electrode; and a contact pressure measuring unit which measures the contact pressure acting in the z axis direction of the upper electrode, wherein each upper electrode of each sensor unit arranged on the same column of the matrix is connected in the column direction in common, and respective lower electrode sides of the x axis shear stress measuring unit, the y axis shear stress measuring unit, and the contact pressure measuring unit of each sensor unit arranged in the same row of the matrix are connected in the row direction in common.

Here, in the distribution measuring sensor of the present invention, wherein each of the x axis shear stress measuring unit and the y axis shear stress measuring unit may have a region where a part of the upper electrode and a part of the lower electrode side of each measuring unit overlap vertically (in the z axis direction), the x axis shear stress measuring unit may measure the shear stress in the x axis direction on the basis of a change in electrical resistance value due to a shear deformation in the x axis direction of the pressure sensitive material in the overlapping region when the shear stress in the x axis direction acts, the y axis shear stress measuring unit may measure the shear stress in the y axis direction on the basis of a change in electrical resistance value due to a shear deformation in the y axis direction of the pressure sensitive material in the overlapping region when the shear stress in the y axis direction acts, and the contact pressure measuring unit may have a region where a part of the upper electrode and all of the lower electrode side of sad contact pressure measuring unit overlap vertically (in the z axis direction), and measures the contact pressure in the z axis direction on the basis of a change in electrical resistance value due to a deformation in the z axis direction of the pressure sensitive material in the overlapping region when the contact pressure in the z axis direction acts.

Here, in the distribution measuring sensor of the present invention, wherein the upper electrode may have a predetermined shape which has an x axis parallel portion having a side parallel to the x axis direction and a y axis parallel portion having a side parallel to the y axis direction, the lower electrode side of the x axis shear stress measuring unit may have a rectangular shape smaller than the upper electrode, and an area of a part of the rectangular shape overlaps the y axis parallel portion vertically (in the z axis direction), the lower electrode side of the y axis shear stress measuring unit may have a rectangular shape smaller than the upper electrode, and an area of a part of the rectangular shape overlaps the x axis parallel portion vertically (in the z axis direction), and the lower electrode side of the contact pressure measuring unit may have a predetermined shape smaller than the upper electrode, and an area of the entire predetermined shape overlaps the upper electrode.

Here, in the distribution measuring sensor of the present invention, wherein a copper-clad polyimide film may be used for the upper electrode and the lower electrode, and a conductive polymer material may be used for the pressure sensitive ingredient.

Here, in the distribution measuring sensor of the present invention, wherein the plane may be an interface between a living body and a solid substance.

A distribution measuring sensor system of the present invention is a distribution measuring sensor system using the distribution measuring sensor according to any one of claims 1 to 5, comprising: a relay unit configured to enable selecting each column line through which each upper electrode of each sensor unit arranged in the same column of the matrix are connected in the column direction in common on the basis of an input selection signal; an inverting amplifier circuit unit constituted of each inverting amplifier circuit whose input side is connected to each row line through which a lower electrode of a contact pressure measuring unit, a lower electrode of an x axis shear stress measuring unit, and a lower electrode of a y axis shear stress measuring unit of each sensor unit arranged in the same row of the matrix are connected in the row direction in common; an A/D conversion unit whose input side is connected to each inverting amplifier circuit constituting the inverting amplifier circuit unit; and a computer connected to an output side of the A/D conversion unit and an input side of the relay unit, wherein a selection signal is output from the computer to the relay unit, a column line is selected by the relay unit on the basis of the selection signal, a power supply voltage supplied to the relay unit is applied to each upper electrode of each sensor unit connected to the column line, a voltage based on each of a contact pressure, an x axis shear stress, and a y axis shear stress acting on the contact pressure measuring unit, the x axis shear stress measuring unit, and the y axis shear stress measuring unit of each sensor unit connected the column line is output to each row line from each lower electrode of each of the contact pressure measuring unit, the x axis shear stress measuring unit, and the y axis shear stress measuring unit, an output voltage from each inverting amplifier circuit of the inverting amplifier circuit unit connected to each row line is output to the A/D conversion unit, an output from the A/D conversion unit is output to the computer, and the computer thus repeats processing the voltage based on the contact pressure, the x axis shear stress, and the y axis shear stress from each sensor unit corresponding to one column selected by the selection signal and outputting a selection signal to select a subsequent column line.

Here, in the distribution measuring sensor system of the present invention, wherein an input side of the A/D conversion unit may be connected to each inverting amplifier circuit constituting the inverting amplifier circuit unit through each switch, and the computer may comprise: selection signal controlling means for outputting a selection signal to select a designated column of the matrix to the relay unit; A/D conversion unit controlling means for sequentially inputting to the A/D conversion unit an output voltage from each inverting amplifier circuit of the inverting amplifier circuit unit based on a contact pressure, an x axis shear stress, and a y axis shear stress from each sensor unit corresponding to one column in regard to a column selected by the selection signal output from the selection signal controlling means by selecting each switch of the A/D conversion unit; voltage data recording means for recording voltage data based on the contact pressure, the x axis shear stress, and the y axis shear stress from each sensor unit which have been input to the A/D conversion unit by the A/D conversion unit controlling means and subjected to A/D conversion by the A/D conversion unit in a contact pressure recording region, an x axis shear stress recording region, and a y axis shear stress recording region for each sensor unit; converting means for converting each voltage data recorded in the contact pressure recording region, the x axis shear stress recording region, and the y axis shear stress recording region for each sensor unit by the voltage data recording means into the contact pressure, the x axis shear stress, and the y axis shear stress acting on each sensor unit on the basis of a relationship according to predetermined measurement principles between the contact pressure, the x axis shear stress, and the y axis shear stress acting on the sensor unit and each output voltage from each inverting amplifier circuit connected to each lower electrode; displaying means for displaying the contact pressure, the x axis shear stress, and the y axis shear stress acting on each sensor unit which have been converted by the converting means in an output display unit of the computer in a predetermined display format; and repeating means for repeating processing from the selection signal controlling means by designating a subsequent column of the column selected by the selection signal output from the selection signal controlling means.

Here, in the distribution measuring sensor system of the present invention, wherein the predetermined measurement principle between the contact pressure acting on the sensor unit and the output voltage from the inverting amplifier circuit connected to the lower electrode in the converting means may be a measurement principle that an output voltage ($V_p$) based on the contact pressure is representable by using a resistance variation ($\Delta R_p$) alone based on the contact pressure like the following Expression 5 (Expression 1 in claims):

[Numerical formula 1]

$$\frac{V_p}{E} = -\frac{R}{(R_0 + \Delta R_p)} \quad (5)$$

where the power supply is (E), the output voltage from the inverting amplifier circuit of the inverting amplifier circuit unit based on the contact pressure is ($V_p$), a feedback resistance of the inverting amplifier circuit is (R), a resistance between the upper electrode and the lower electrode at the time of no load of a pressure ($R_0$), and the resistance variation between the upper electrode and the lower electrode at the time of loading of the contact pressure is ($\Delta R_p$).

Here, in the distribution measuring sensor system of the present invention, wherein the predetermined measurement principle between the x axis shear stress or the y axis shear stress acting on the sensor unit and each output voltage from each inverting amplifier circuit connected to the lower electrode in the converting means may be a measurement principle that an output voltage ($V_p$) based on the contact pressure and an output voltage ($V_\tau$) based on the shear stress are representable by using a resistance variation ($\Delta R_\tau$) alone based on the shear stress like the following Expression 6 (Expression 2 in claims):

[Numerical formula 2]

$$\left(\frac{1}{V_\tau} - \frac{1}{V_p}\right) \times E = -\frac{\Delta R_\tau}{R} \quad (6)$$

where the output voltage is (E), the output voltage from the inverting amplifier circuit of the inverting amplifier circuit unit based on the contact pressure is ($V_p$), the output voltage from the inverting amplifier circuit of the inverting amplifier circuit unit based on the shear stress is (Vτ: a generic term for $V_{τx}$ corresponding to the x axis and $V_{τy}$ corresponding to they axis), a feedback resistance of the inverting amplifier circuit is (R), and the resistance variation between the upper electrode and the lower electrode at the time of loading of the shear stress is ($ΔR_τ$: a generic term for $ΔR_{τx}$ corresponding to the x axis and $ΔR_{τy}$ corresponding to the y axis).

Here, in the distribution measuring sensor system of the present invention, wherein the predetermined display format in the displaying means may arrange indications of the sensor units in correspondence with the matrix, may show magnitude of the contact pressure by using each predetermined color in accordance with each sensor unit, and may show shear stress which is a combination of the x axis shear stress and the y axis shear stress by using a vector.

A distribution measuring program of the present invention is a distribution measuring program which operates the computer in the distribution measuring sensor system according to any one of claims 6 to 10, the distribution measuring program configured to allow the computer to execute: a selection signal controlling step of outputting a selection signal to select a designated column of the matrix to the relay unit; an A/D conversion unit controlling step of sequentially inputting to the A/D conversion unit an output voltage from each inverting amplifier circuit of the inverting amplifier circuit unit based on a contact pressure, an x axis shear stress, and a y axis shear stress from each sensor unit corresponding to one column by selecting each switch of the A/D conversion unit with regard to the column selected by the selection signal output at the selection signal controlling step; a voltage data recording step of recording voltage data based on the contact pressure, the x axis shear stress, and the y axis shear stress from each sensor which have been input to the A/D conversion unit and subjected to A/D conversion by the A/D conversion unit at the A/D conversion unit controlling step in a contact pressure recording region, an x axis shear stress recording region, and a y axis shear stress recording region for each sensor unit; a converting step of converting each voltage data recorded in the contact pressure recording region, the x axis shear stress recording region, and the y axis shear stress recording region for each sensor unit at the voltage data recording step into the contact pressure, the x axis shear stress, and the y axis shear stress acting on each sensor unit on the basis of a relationship according to predetermined measurement principles between the contact pressure, the x axis shear stress, and the axis shear stress acting on the sensor unit and each output voltage from each inverting amplifier circuit connected to the each lower electrode; a displaying step of displaying the contact pressure, the x axis shear stress, and the y axis shear stress acting on each sensor unit which have been converted at the converting step in an output display unit of the computer in a predetermined display format; and a repeating step for repeating processing from the selection signal controlling step by designating a subsequent column of the column selected by the selection signal output at the selection signal controlling step.

A recording medium of the present invention is a recording medium readable by a computer that records the distribution measuring program of the present invention.

Effects of the Invention

The distribution measuring sensor according to the present invention has a structure in which a sensor unit which measures a shear stress in each axis direction (an x axis, a y axis) of a plane and a contact pressure in an axis (a z axis) direction perpendicular to the plane is arranged at each element of a matrix. The sensor unit is constituted of an upper electrode and a lower electrode which is arranged below the upper electrode through a pressure sensitive material. In the respective sensor units in the x axis direction which are arranged in the same column of the matrix, the respective upper electrodes are connected in a column direction (the x axis direction) in common through a connecting line. In the respective sensor units in the y axis direction which are arranged in the same row of the matrix, the respective lower electrodes are connected in a row direction (the y axis direction) in common through a different connecting line. In a region where the upper electrode and the lower electrode overlap in an up-and-down direction (the z axis direction), each sensor unit includes an x axis shear stress measuring unit which measures a shear stress in the x axis direction acting between the upper electrode and the lower electrode, a y axis shear stress measuring unit which measures a shear stress in the y axis direction acting between the upper electrode and the lower electrode, and a contact pressure measuring unit which measures a contact pressure acting in the z axis direction of the upper electrode. The upper electrode is used for the measurement of the shear stress and the measurement of the contact pressure in common.

According to the structure of the sensor unit of the present invention mentioned above, the contact pressure measuring unit can detect the contract pressure in the z axis direction alone without interference with the shear stress in the x axis direction and the shear stress in the y axis direction. Thus, the effect which enables the simultaneous measurement of the contact pressure and both the x axis shear stress and the y axis shear stress can be provided.

As described above, the distribution measuring sensor according to the present invention has many sensor units (measurement points) coupled through the respective common connecting lines, whereby many measurement points are arranged at intersection points (elements of the matrix) of the upper and lower electrodes. This matrix-shaped structure enables acquiring information of the sensor units (the intersection points) by sequentially selecting the respective rows in a state where one column of the matrix is selected rather than scanning the measurement points one by one to obtain information of the contact pressure and the shear stress. Further, it is possible to provide the effect which enables performing matrix type scanning to obtain information of the sensor units by selecting a next column with the use of a repetition unit like a previously selected column.

Thus, the distribution measuring sensor system of the present invention has the effect of providing a distribution measuring sensor system which has characteristics as the thin flexible distribution measurement sensor applicable to the measurement of the contact pressure and the shear stress acting on an interface between a living body (a finger) and an object (a container), can greatly reduce a wiring region even if many sensor units are integrated to grasp a distribution of a tactile sense, simplify a design, suppress an increase in manufacturing costs, and has a high resolution.

MODE(S) FOR CARRYING OUT THE INVENTION

Each embodiment will now be described hereinafter in detail with reference to the drawings.

Embodiment 1

Figure 1:
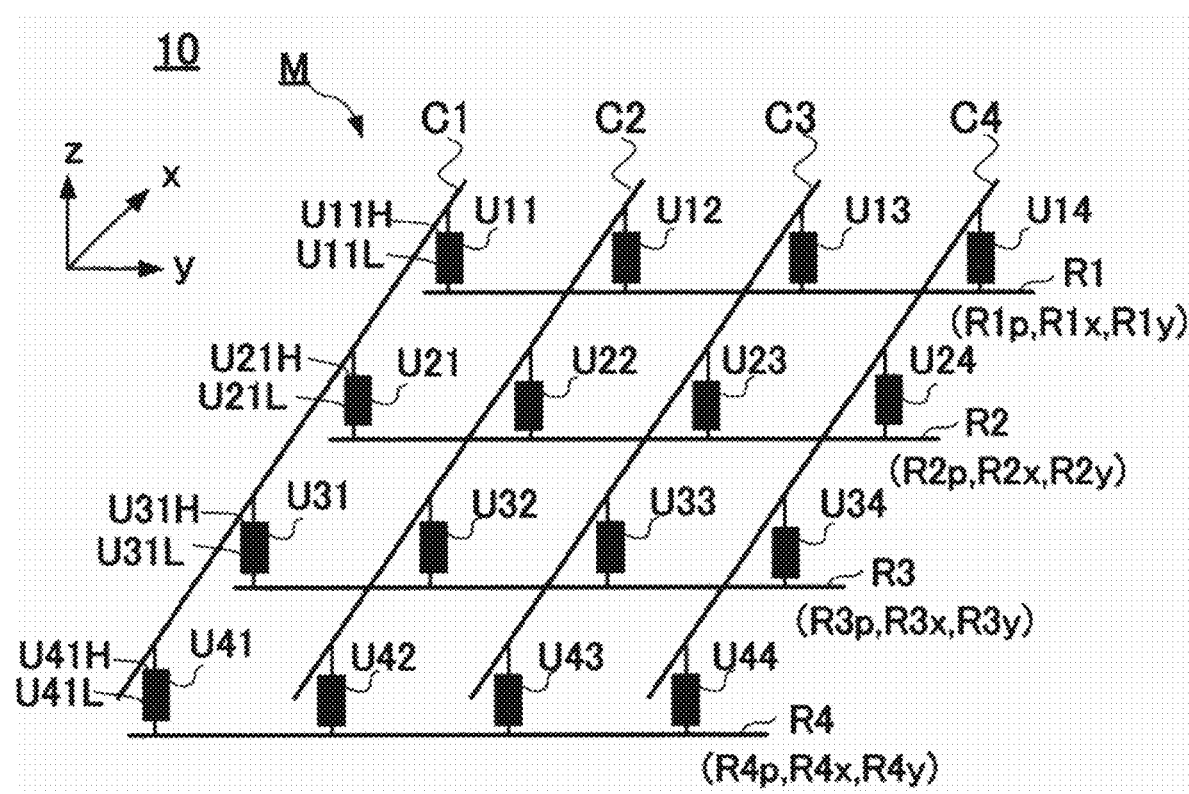
FIG. 1 shows a distribution measuring sensor 10 according to the present invention.

FIG. 1 shows a distribution measuring sensor 10 according to the present invention. As shown in FIG. 1, the distribution measuring sensor 10 has a structure in which a sensor unit Uij which measures a shear stress in each axis (an x axis, a y axis) direction of a plane and a contact pressure in an axis (a z axis) direction perpendicular to the plane is arranged at each element of a matrix M. The directions of the x, y, and z axes are as indicated by coordinate axes shown in FIG. 1, and the direction of each axis will be appropriately indicated by each coordinate axis in each following drawing. In the matrix M of the sensor units Uij shown in FIG. 1, Uij (a row i=1 to 4, a column j=1 to 4) is exemplified, but the number of rows and the number of columns in the matrix M are not restricted to 4×4. The sensor unit Uij shown in FIG. 1, e.g., a sensor unit U11 is constituted of an upper electrode U11H and a lower electrode U11L arranged below the upper electrode U11H through a pressure sensitive material (not shown in FIG. 1). Each of sensor units U21, U31, and U41 present in the same column as the sensor unit U11 is likewise constituted of an upper electrode U21H and a lower electrode U21L, an upper electrode U31H and a lower electrode U31L, or an upper electrode U41H and a lower electrode U41L. Other sensor units Uij (i=1 to 4, j=2 to 4) are the same, and reference signs of the upper electrodes and the lower electrodes are omitted for the sake of drawings. As shown in FIG. 1, the respective sensor units Uij (i=1 to 4) in the x axis direction arranged in the same column j in the matrix M have the respective upper electrodes UijH (i=1 to 4) connected in a column j direction (the x axis direction) in common through a connecting line Cj. In addition, as shown in FIG. 1, the respective sensor units Uij (j=1 to 4) in the y axis direction arranged in the same row i in the matrix M have the respective lower electrodes UijL (j=1 to 4) connected in a row i direction (the y axis direction) in common through a connecting line Ri.

As will be described later, each sensor unit Uij (i=1 to 4, j=1 to 4) includes an x axis shear stress measuring unit which measures a shear stress in the x axis direction acting between the upper electrode UijH (i=1 to 4, j=1 to 4) and the lower electrode UijL (i=1 to 4, j=1 to 4), a y axis shear stress measuring unit which measures a shear stress in the y axis direction acting between the upper electrode UijH (i=1 to 4, j=1 to 4) and the lower electrode UijL (i=1 to 4, j=1 to 4), and a contact pressure measuring unit which measures a contact pressure acting in the z axis direction of the upper electrode UijH (i=1 to 4, j=1 to 4) in a region where the upper electrode UijH (i=1 to 4, j=1 to 4) and the lower electrode UijL (i=1 to 4, j=1 to 4) overlap in an up-and-down direction (the z axis direction). As shown in FIG. 1, the respective sensor units Uij (j=1 to 4) arranged in the same row i in the matrix M have electrodes (later described UijLx, UijLy, and UijLp) constituting the x axis shear stress measuring units, they axis shear stress measuring units, and the contact pressure measuring units in the respective lower electrodes UijL (j=1 to 4) connected in the row i direction in common through respective connecting lines Rix, Riy, and Rip.

Figure 2:
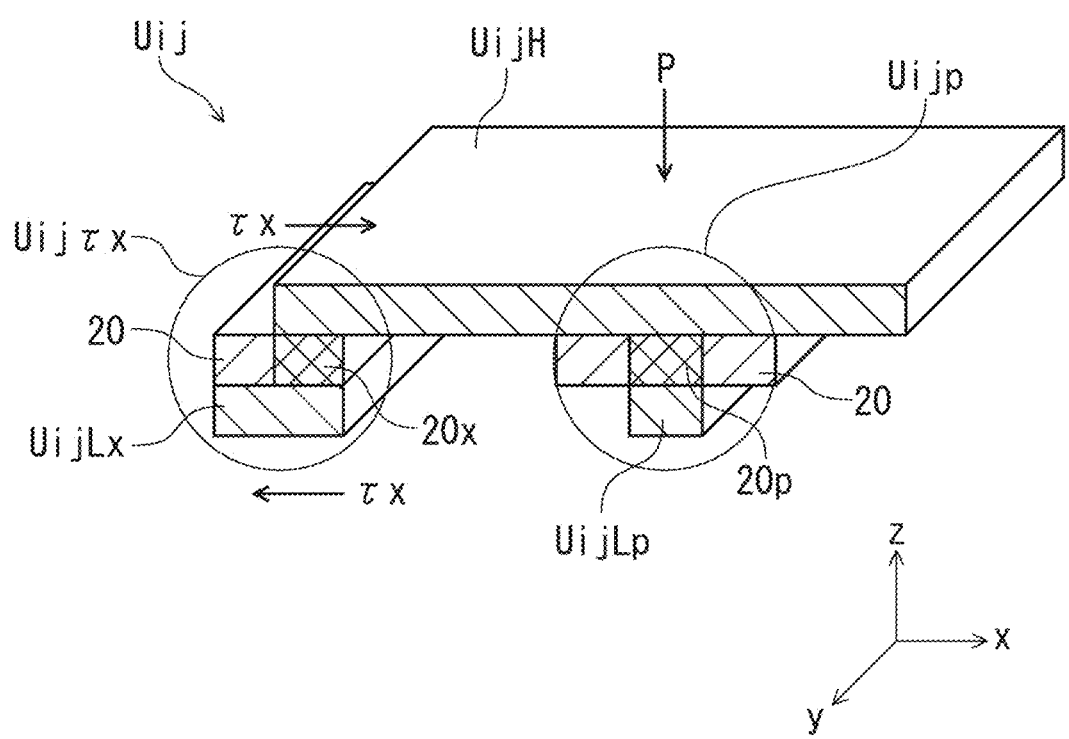
FIG. 2 shows a perspective view of an enlarged sensor unit Uij.

FIG. 2 shows a perspective view of an enlarged sensor unit Uij. In FIG. 2, parts with the same reference signs as those in FIG. 1 denote the same elements, and hence a description thereof will be omitted. In FIG. 2, a reference sign Uijp denotes a contact pressure measuring unit (enclosed with a circle), UijLp designates a lower electrode constituting the contact pressure measuring unit Uijp, and p represents a contact pressure acting on the upper electrode UijH in the z axis direction. Furthermore, a reference sign Uijτx denotes an x axis shear stress measuring unit (enclosed with a circle), UijLx designates a lower electrode constituting the x axis shear stress measuring unit Uijτx, and τx represents a shear stress in the x axis direction acting between the upper electrode UijH and the lower electrode UijLx. In FIG. 2, reference signs 20, 20x, and 20p denote pressure sensitive materials, and the upper electrode UijH is arranged to face the left and right lower electrodes UijLx and UijLp through the pressure sensitive material 20. The upper electrode UijH is used for measurement of the shear stress τx (the x axis shear stress measuring unit Uijτx) and measurement of the contact pressure p (the contact pressure measuring unit Uijp) in common. The pressure sensitive materials 20x and 20p shown in FIG. 2 represent the pressure sensitive material 20 in a region where the upper electrode UijH (i=1 to 4, j=1 to 4) and the lower electrode UijL (i=1 to 4, j=1 to 4) overlap vertically (in the z axis direction). More specifically, the pressure sensitive material 20x represents the pressure sensitive material 20 in a region where a part of the upper electrode UijH and a part of the lower electrode UijLx overlap in the z axis direction in the x axis shear stress measuring unit Uijτx, and the pressure sensitive material 20p represents the pressure sensitive material 20 in a region where a part of the upper electrode UijH and all of the lower electrode UijLp overlap in the z axis direction in the contact pressure measuring unit Uijp. The pressure sensitive materials 20, 20x, and 20p are pressure conversion elements for the shear stress and the contact pressure, and polythiophene which is a conductive polymer material is used. Polythiophene has characteristics that an electrical resistance in a thickness direction varies depending on an acting pressure. More specifically, it has properties that conductivity rises in accordance with application of an acting pressure. Although the shear stress in the y axis direction and the y axis shear stress measuring unit are the same as the shear stress τx in the x axis direction and the x axis shear stress measuring unit Uijτx except that they are different in direction alone, they are omitted in the drawing for the sake of convenience, and a description thereof will be given later.

FIGS. 3(A) and (B) are vertical cross-sectional views of the vicinity of the x axis shear stress measuring unit Uijτx of the sensor unit Uij shown in FIG. 2, parts with the same reference signs as those in FIG. 2 denote the same elements, and hence a description thereof will be omitted. As shown in FIG. 3(A), a distance between the upper electrode UijH and the lower electrode UijLx in the thickness direction in the pressure sensitive material 20x of the x axis shear stress measuring unit Uijτx is r. Here, when the shear stress τx acts on the x axis shear stress measuring unit Uijτx in the x axis direction, the upper electrode UijH side shifts toward a positive direction of the x axis and the lower electrode UijLx side shifts toward a negative direction of the x axis as shown in FIG. 3(B). As a result of the shifts of both the electrodes (a change in positional relationship), a shear deformation in the x axis direction occurs in the pressure sensitive material 20x part as show in FIG. 3(B). Consequently, in the pressure sensitive material 20x part, the distance between the upper electrode UijH and the lower electrode UijLx in the thickness direction becomes rτ larger than the original distance r, and hence an electrical resistance in the x axis shear stress measuring unit Uijτx increases.

Figure 4:
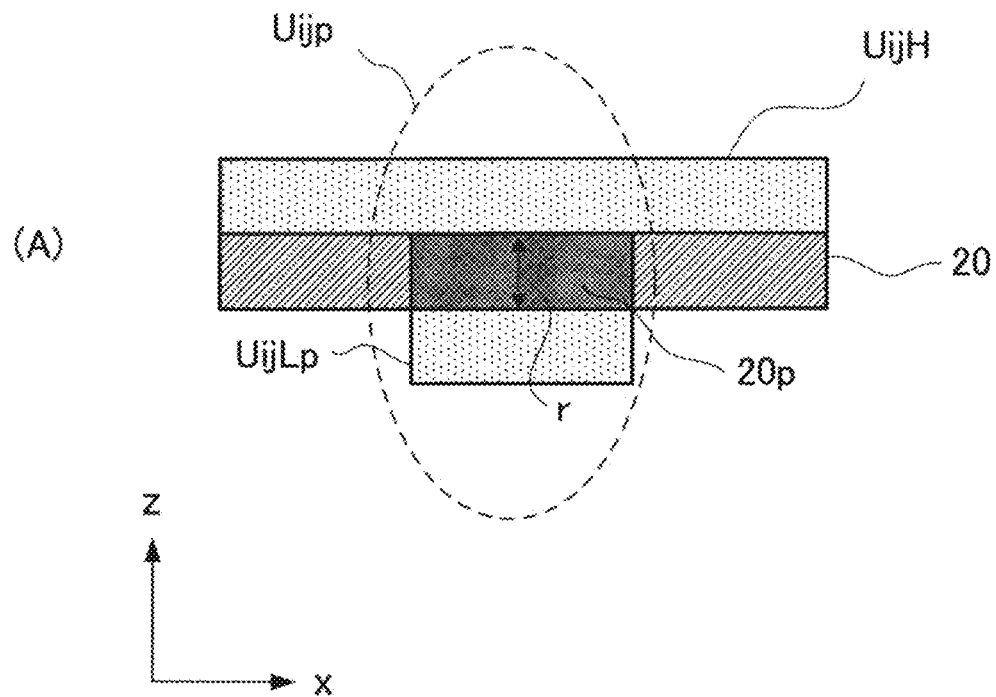
FIGS. 4(A) and (B) are vertical cross-sectional views of the vicinity of the contact pressure measuring unit Uijp of the sensor unit Uij shown in FIG.
Figure 4:
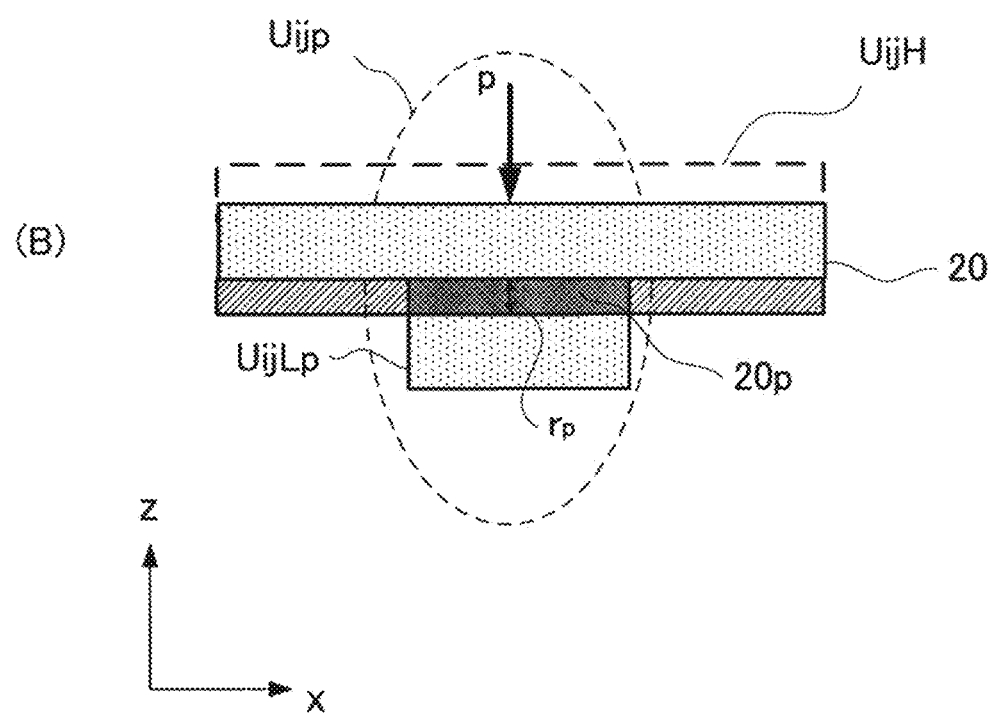

FIGS. 4(A) and (B) are vertical cross-sectional views of the vicinity of the contact pressure measuring unit Uijp of the sensor unit Uij shown in FIG. 2, parts with the same reference signs as those in FIG. 2 denote the same elements, and hence a description thereof will be omitted. As shown in FIG. 4(A), a distance between the upper electrode UijH and the lower electrode UijLp in the thickness direction in the pressure sensitive material 20p of the contact pressure measuring unit Uijp is r. Here, when the contact pressure p acts on the contact pressure measuring unit Uijp in the z axis direction, a deformation in the z axis direction occurs in the pressure sensitive material 20p part as shown in FIG. 4(B). Consequently, in the pressure sensitive material 20p part, the distance between the upper electrode UijH and the lower electrode UijLp in the thickness direction becomes rp which is smaller than the original distance r, and hence an electrical resistance in the contact pressure measuring unit Uijp decreases.

Figure 5:
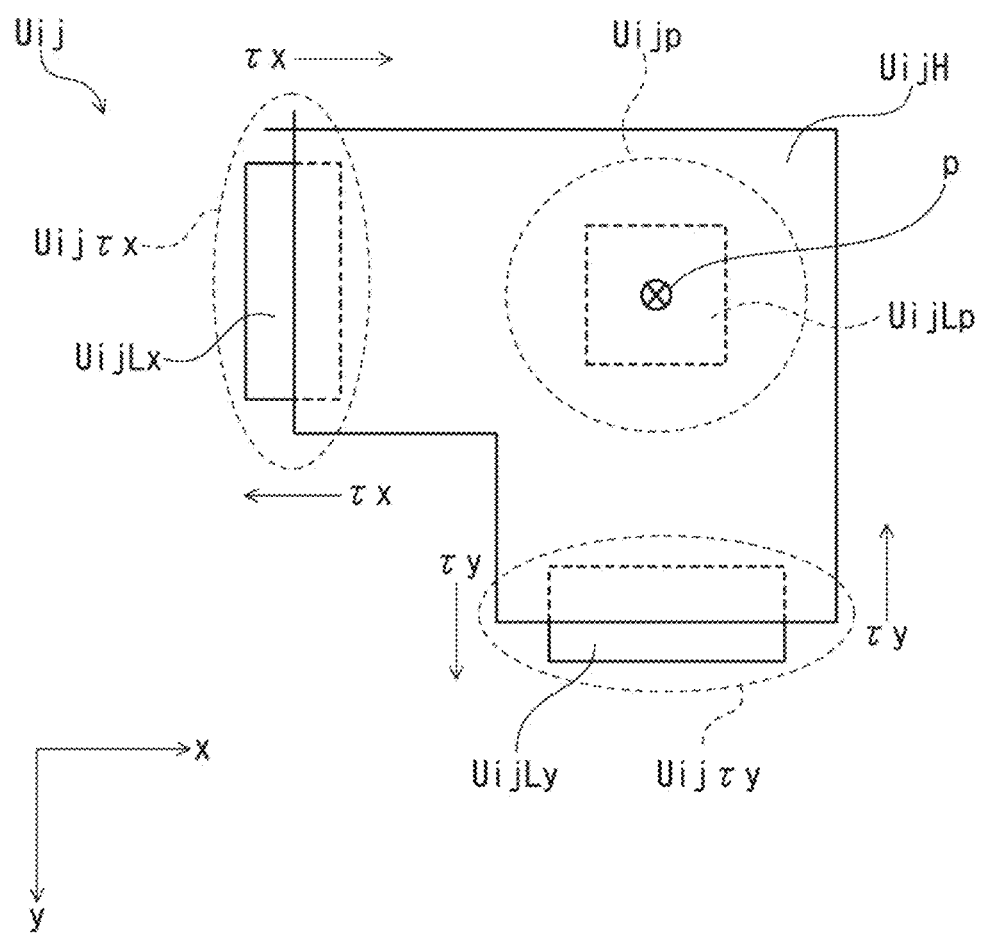
FIG. 5 shows a shape example of the sensor unit Uij in a plan view.

FIG. 5 shows a shape example of the sensor unit Uij in a plan view. In FIG. 5, parts with the same reference signs as those in FIG. 2 denote the same elements, and hence a description thereof will be omitted. In FIG. 5, each invisible electrode (or a part of each electrode) which is present below the upper electrode UijH is indicated by a dotted line, and each lead line to the invisible electrodes or the like is also indicated by a dotted line (the same applies hereafter). FIG. 5 shows a shear stress τy in the y axis direction, a y axis shear stress measuring unit Uijτy (it is enclosed with a dotted circle. Each lead line to the dotted circle is also indicated by a dotted line. The same applies to Uijτx and Uijp hereafter), and the lower electrode UijLy. As exemplified in FIG. 5, the upper electrode UijH has a square shape lacking a lower left corner (a predetermined shape). The upper electrode UijH has an x axis parallel portion having a side parallel to the x axis direction (a portion near a lower right side of the upper electrode UijH. A portion near an end side of the upper electrode UijH constituting the y axis shear stress measuring unit Uijτy) a day axis parallel portion having a side parallel to they axis direction (a portion near an upper left side of the upper electrode UijH. A portion near an end side of the upper electrode UijH constituting the x axis shear stress measuring unit Uijτx).

As shown in FIG. 5, the lower electrode UijLx has an oblong (a rectangular shape) shape smaller than the upper electrode UijH, and it was designed in such a manner that an area (which is preferably a half area) of a part of the lower electrode UijLx overlaps an area of a part of the upper electrode UijH vertically (in the z axis direction) in the y axis parallel portion of the upper electrode UijH. The half area becomes the above-described overlapping region in a case where the shear stress τx does not act in the x axis direction. Here, when the shear stress τx acts between the upper electrode UijH and the lower electrode UijLx, the distance r in the thickness direction changes to rτ (>r) due to a shear deformation of the pressure sensitive material 20 in the x axis direction in the overlapping region as described above (see FIGS. 3(A) and (B)). Consequently, an electrical resistance value between the upper electrode UijH and the lower electrode UijLx in the shear stress measuring unit Uijτx changes, and hence the shear stress measuring unit Uijτx can measure the shear stress τx in the x axis direction.

As shown in FIG. 5, the lower electrode UijLy (the lower electrode UijL side portion constituting the y axis shear stress measuring Uijτy unit) also has an oblong (rectangular) shape smaller than the upper electrode UijH like the lower electrode UijLx, and it was designed in such a manner that an area (which is preferably a half area) of a part of the lower electrode UijLy overlaps an area of a part of the upper electrode UijH vertically (in the z axis direction) in the x axis parallel portion of the upper electrode UijH. The half area becomes the overlapping region in a case where the shear stress τy does not act in the y axis direction. Here, when the shear stress τy acts between the upper electrode UijH and the lower electrode UijLy, the distance r in the thickness direction changes to rτ (>r) due to a shear deformation of the pressure sensitive material 20y (not shown) in the y axis direction in the overlapping region as described above (see FIGS. 3(A) and (B) while replacing the x axis with the y axis). Consequently, an electrical resistance value between the upper electrode UijH and the lower electrode UijLy in the shear stress measuring unit Uijτy changes, and hence the shear stress measuring unit Uijτy can measure the shear stress τy in the y axis direction.

When the shear stress τy in the y axis direction acts on the x axis shear stress measuring unit Uijτx, a mutual positional displacement in the y axis direction occurs in the overlapping region in the x axis shear stress measuring unit Uijτx, but a shear deformation in the x axis direction does not occur. That is, the electrical resistance value between the upper electrode UijH and the lower electrode UijLx in the x axis shear stress measuring unit Uijτx does not change. Thus, the x axis shear stress measuring unit Uijτx can detect the shear stress τx in the x axis direction alone without being interfered with the shear stress τy in the y axis direction. Likewise, when the shear stress τx in the x axis direction acts on the y axis shear stress measuring unit Uijτy, a mutual positional displacement occurs in the x axis direction in the overlapping region in the y axis shear stress measuring unit Uijτy, but a shear deformation in the y axis direction does not occur. That is, the electrical resistance value between the upper electrode UijH and the lower electrode UijLy in the y axis shear stress measuring unit Uijτy does not change. Thus, the y axis shear stress measuring unit Uijτy can detect the shear stress τy in the y axis direction alone without being interfered with the shear stress τx in the x axis direction. Therefore, when a shear stress τm (not shown) having arbitrary xy directions acts between the upper electrode UijH and the lower electrodes UijL (the lower electrodes UijLx and UijLy), a component τmx (not shown) in the x axis direction of the shear stress τm and a component τmy (not shown) in the y axis direction of the shear stress τm act on the pressure sensitive materials 20x and 20y in the overlapping region, respectively. Consequently, the electrical resistance value between the upper electrode UijH and the lower electrode UijLx in the shear stress measuring unit Uijτx changes in accordance with the shear stress τmx, and hence the shear stress measuring unit Uijτx can measure the shear stress τmx in the x axis direction. Likewise, the electrical resistance value between the upper electrode UijH and the lower electrode UijLy in the shear stress measuring unit Uijτy changes in accordance with the shear stress τmy, and hence the shear stress measuring unit Uijτy can measure the shear stress τmy in the y axis direction. Thus, on the basis of the measured shear stresses τmx and τmy, magnitude and an acting direction of the shear stress τm can be discriminated.

As shown in FIG. 5, the lower electrode UijLp of the contact pressure measuring unit Uijp has a square shape (a predetermined shape), and it was designed in such a manner that an entire area of this shape overlaps an area of a part of the upper electrode UijH vertically (in the z axis direction) in a middle portion of the upper electrode UijH. The area becomes the overlapping region in a case where the contact pressure p does not act in the z axis direction.

Here, when the contact pressure p acts between the upper electrode UijH and the lower electrode UijLp, the distance r in the thickness direction changes to rp (<r) due to a deformation of the pressure sensitive material 20p in the z axis direction in the overlapping region as described above (see FIGS. 4(A) and (B)). Consequently, the electrical resistance value between the upper electrode UijH and the lower electrode UijLp in the contact pressure measuring unit Uijp changes, and hence the contact pressure measuring unit Uijp can measure the contact pressure p in the z axis direction.

When the shear stress τx in the x axis direction and the shear stress τy in the y axis direction act on the contact pressure measuring unit Uijp, a mutual positional displacement occurs in the x and y axis directions in the overlapping region in the contact pressure measuring unit Uijp, but a side system in the z axis direction is not produced. That is, the electrical resistance value between the upper electrode UijH and the lower electrode UijLp in the contact pressure measuring unit Uijp does not change. Therefore, the contact pressure measuring unit Uijp can detect the contact pressure p in the z axis direction alone without being interfered with the shear stress τx in the x axis direction and the shear stress τy in the y axis direction. Thus, the contact pressure p can be measured simultaneously with the x axis shear stress τx or the y axis shear stress τy.

As described above, the lower electrode UijL is constituted of the lower electrodes UijLp, UijLx, and UijLy which are individually used for the measurement of each of the contact pressure p and the shear stresses τx and τy. On the other hand, the upper electrode UijH is used for the measurement of the contact pressure p and the shear stresses τx and τy in common.

As described above, the upper electrode UijH exemplified in FIG. 5 has the square shape lacking the lower left corner. This is a selection in design to match a length of a long side of the rectangular of the lower electrode UijLx with a length of the y axis parallel portion and to match a length of a long side of the rectangular of the lower electrode UijLy with a length of the x axis parallel portion (and to connect the lower electrode UijL of each sensor unit Uij which will be described later), and the shape of the upper electrode UijH of the sensor unit Uij in the present invention is not restricted to the shape lacking the lower left corner.

Figure 6:
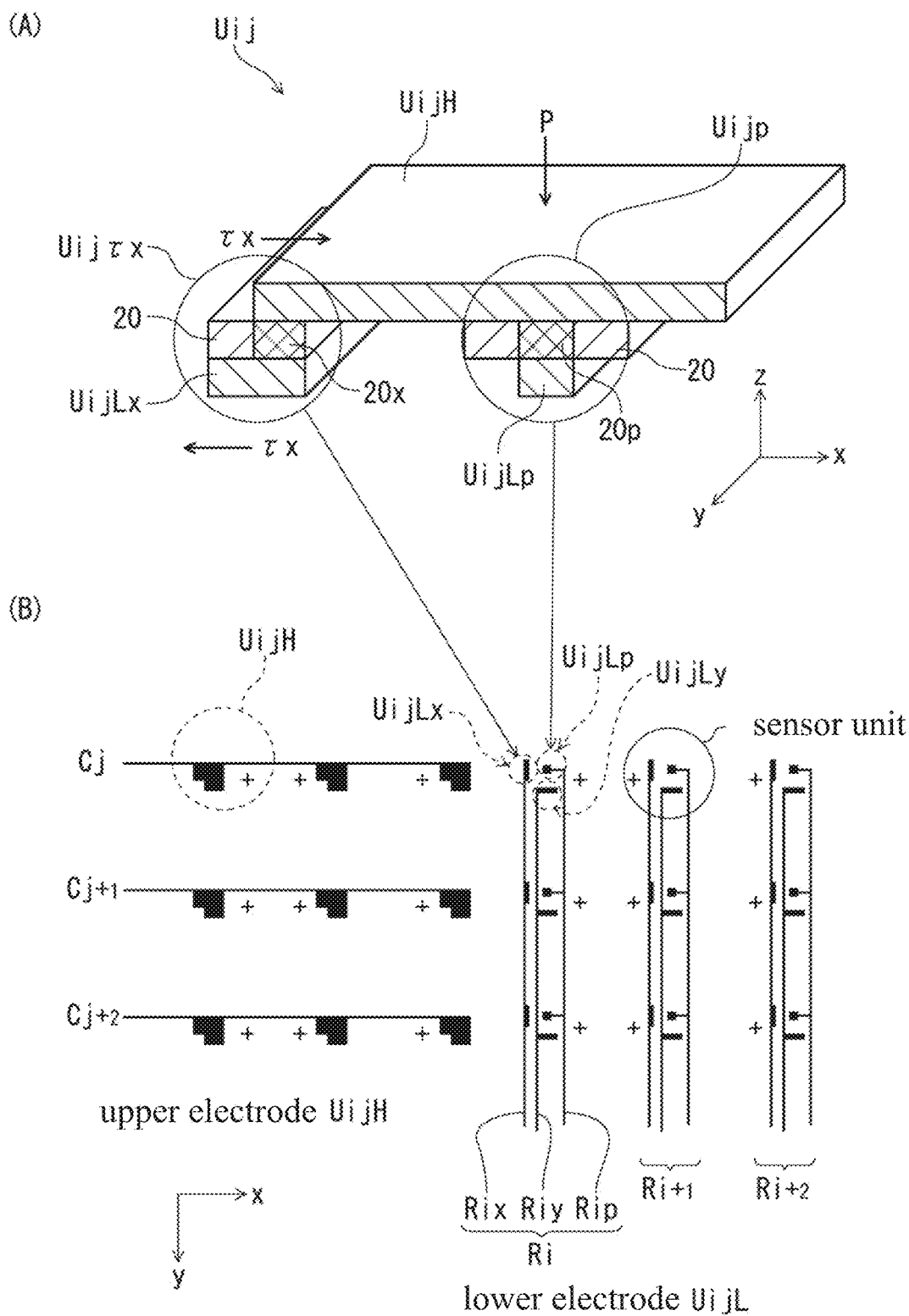
FIG. 6 show an enlarged perspective view (FIG. 6(A)) of the sensor unit Uij shown in FIG. 2 and electrode patterns of the upper electrodes UijH and the lower electrodes UijL associated therewith.

FIG. 6 show an enlarged perspective view (FIG. 6(A)) of the sensor unit Uij shown in FIG. 2 and electrode patterns of the upper electrodes UijH and the lower electrodes UijL associated therewith. In FIGS. 6(A) and (B), parts with the same reference signs as those in FIGS. 1, 2, and 5 denote the same elements, and hence a description thereof will be omitted. The upper electrode UijH shown in FIG. 6(A) is formed at such as position as indicated by a broken line circle in the electrode pattern shown on a left side of FIG. 6(B), and it has a square shape lacking a lower left corner like the upper electrode UijH shown in FIG. 5. As shown on the left side of FIG. 6(B), the respective upper electrodes UijH are connected in a column j direction (the x axis direction) in common through a common connecting line Cj. The lower electrode UijLx shown in FIG. 6(A) is formed at such a position as indicated by an arrow in the electrode pattern on a right side of FIG. 6(B), and has such a rectangular shape as shown in FIG. 5. As shown on the right side of FIG. 6(B), the respective lower electrodes UijLx are connected in a row i direction (the y axis direction) in common through a connecting line Rix. Although not shown in FIG. 6(A), the lower electrode UijLy is formed at such a position as indicated by an arrow in the electrode pattern on the right side of FIG. 6(B), and has such a rectangular shape as shown in FIG. 5. As shown on the right side of FIG. 6(B), the respective lower electrodes UijLy are connected in the row i direction (the y axis direction) in common through a connecting line Riy. The lower electrode UijLp shown in FIG. 6(A) is formed at such a position as indicated by an arrow in the electrode pattern on the right side of FIG. 6(B), and has such a square shape as shown in FIG. 5. As shown on the right side of FIG. 6(B), the respective lower electrodes UijLp are connected in the row i direction (they axis direction) in common through a connecting line Rip.

A copper-clad polyimide film was used as an electrode material of the upper electrodes UijH and the lower electrodes UijL shown in FIGS. 6(A) and (B), and the upper electrodes UijH and the lower electrodes UijL were formed by a wet etching treatment, respectively. As described above, polythiophene which is a conductive polymer material is used for the pressure sensitive materials 20, 20$x$, 20$y$, and 20$p$, the polythiophene was applied to the upper electrodes UijH and the lower electrodes UijL by using a screen printing method, and then the upper electrodes UijH and the lower electrodes UijL were bonded through a protective film. The distribution measuring sensor 10 was fabricated to have a thickness of 300 μm. A size of each sensor unit Uij (a measurement region of one point) is 5.0×5.0 mm$^2$ as a whole, and the lower electrode UijLp of the contact pressure measuring unit Uijp was set to 0.7×0.7 mm$^2$ as a square electrode and each of the lower electrode UijLx of the shear stress measuring unit τx and the lower electrode UijLy of the shear stress measuring unit τy was set to 0.5×1.96 mm$^2$ as a rectangular electrode in each unit. However, the size is an example, and the thickness of the distribution measuring sensor 10, the size of the entire sensor unit Uij, and the size of each of the lower electrodes UijLp, UijLx, and UijLy are not restricted to the above-described sizes.

Figure 7:
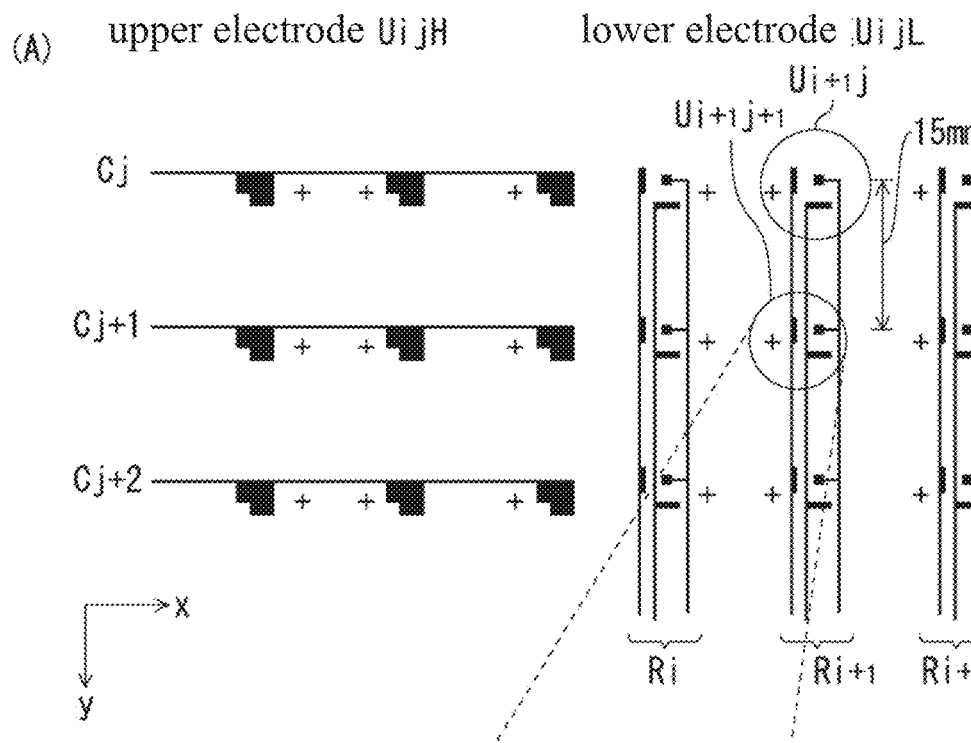
FIG. 7 show electrode patterns (FIG. 7(A)) of the upper electrode UijH and the lower electrode UijL shown in FIG. 6(B) and an enlarged view (FIG. 7(B)) of a part (a sensor unit Ui+1 j+1) of the electrode pattern of the lower electrode UijL.
Figure 7:
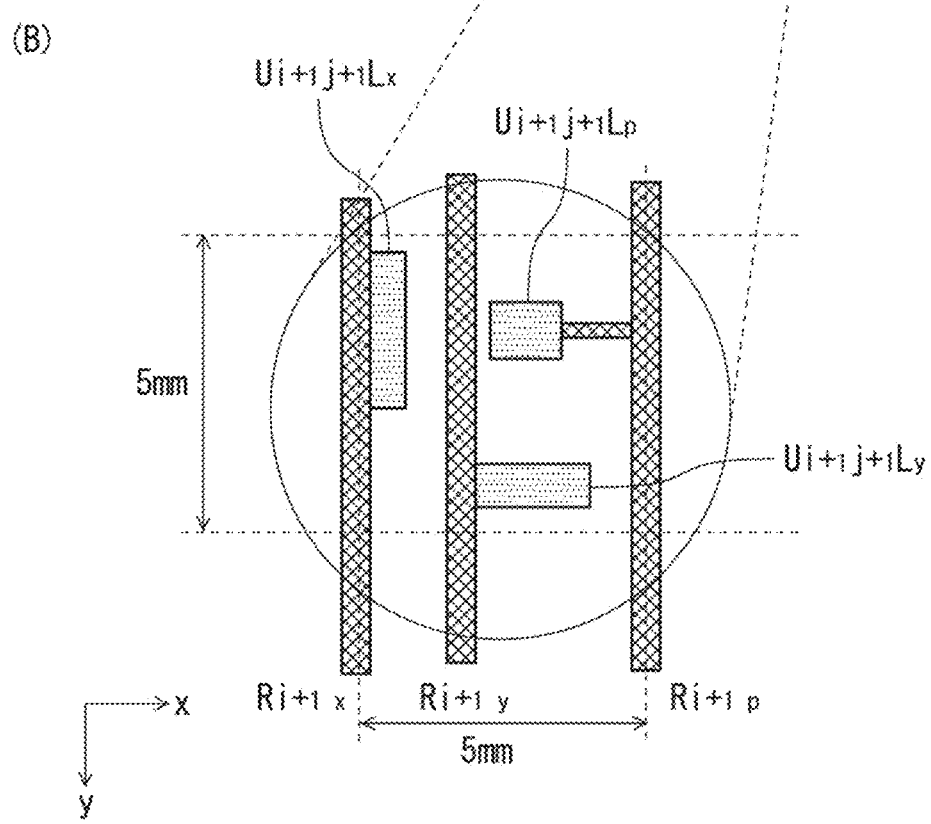

FIG. 7 show electrode patterns (FIG. 7(A)) of the upper electrode UijH and the lower electrode UijL shown in FIG. 6(B) and an enlarged view (FIG. 7(B)) of a part (a sensor unit Ui+1 j+1) of the electrode pattern of the lower electrode UijL. In FIGS. 7(A) and (B), parts with the same reference signs as those in FIGS. 1, 5, and 6 denote the same elements, and hence a description thereof will be omitted. As shown in FIG. 7(A), a distance between sensor units (between the sensor unit Ui+1 j and the sensor unit Ui+1 j+1 as an example) was set to 15 mm. As shown in FIG. 7(B), a size of each sensor unit Uij (the sensor unit Ui+1 j+1 is taken as an example) which is a measurement region of one point was set to 5.0×5.0 mm$^2$ as a whole.

Figure 8:
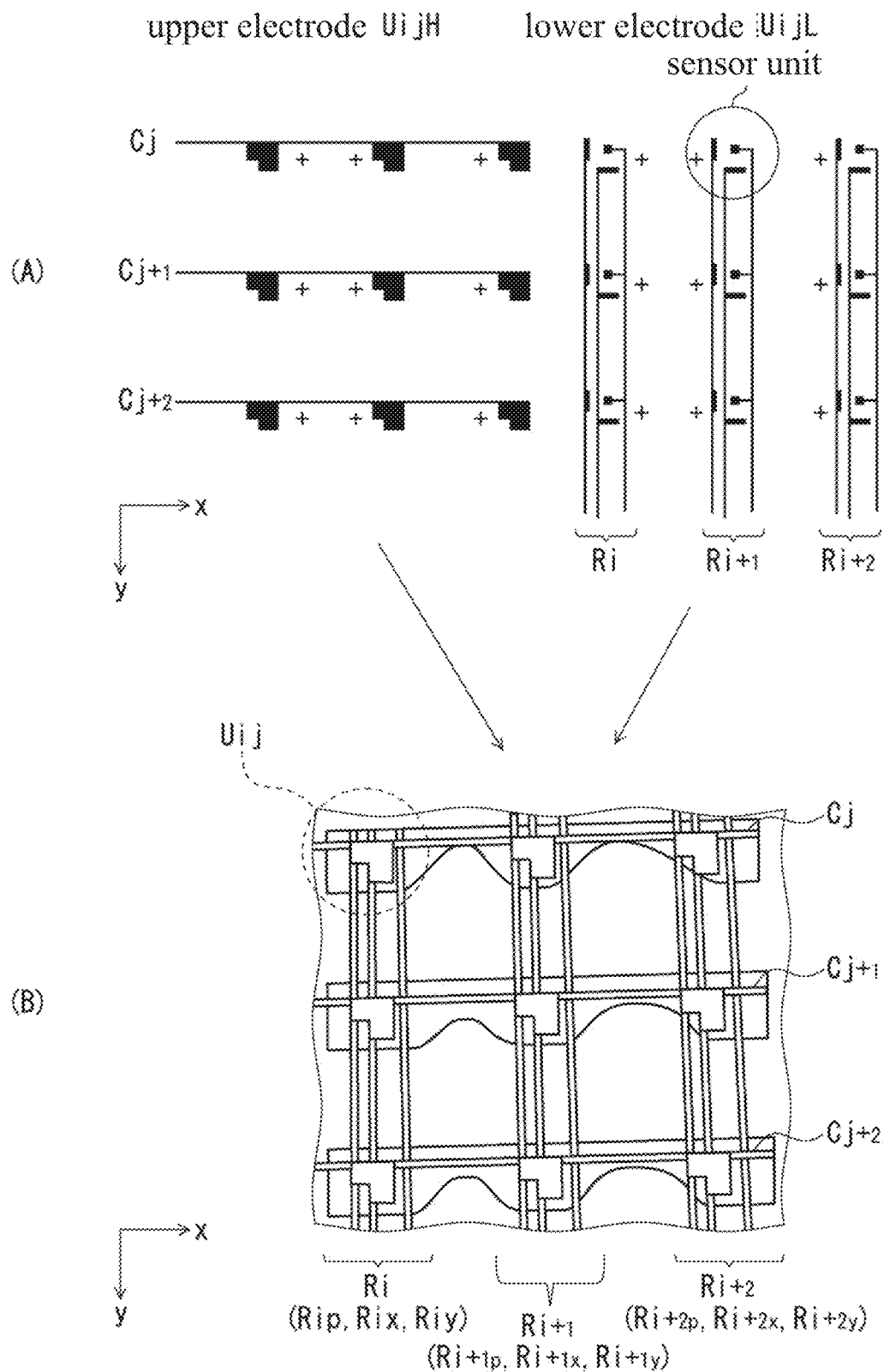
FIG. 8 show electrode patterns (FIG. 8(A)) of the upper electrode UijH and the lower electrode UijL shown in FIG. 6(B) and a state (FIG. 8(B)) where the respective electrode patterns of the upper electrode UijH and the lower electrode UijL are overlapped vertically (the z axis direction. A direction perpendicular to a paper surface).

FIG. 8 show electrode patterns (FIG. 8(A)) of the upper electrode UijH and the lower electrode UijL shown in FIG. 6(B) and a state (FIG. 8(B)) where the respective electrode patterns of the upper electrode UijH and the lower electrode UijL are overlapped vertically (the z axis direction. A direction perpendicular to a paper surface). In FIGS. 8(A) and (B), parts with the same reference signs as those in FIGS. 1, 2, 5, and 6 represent the same elements, and hence a description will be omitted. As shown in FIG. 8(B), the upper electrodes UijH of each sensor unit Uij are connected in the column j direction (the x axis direction) in common through the connecting line Cj. The respective lower electrodes UijL of each sensor unit Uij are connected in the row i direction (the y axis direction) in common through the connecting line Ri. More specifically, the respective lower electrodes UijLx are connected in the row i direction (the y axis direction) in common through a connecting line Rix, the respective lower electrodes UijLy are connected in the row i direction (the y axis direction) in common through a connecting line Riy, and the respective lower electrodes UijLp are connected in the row i direction (the y axis direction) in common through a connecting line Rip. The same applies to the other sensor units, and hence a description thereof will be omitted.

Figure 9:
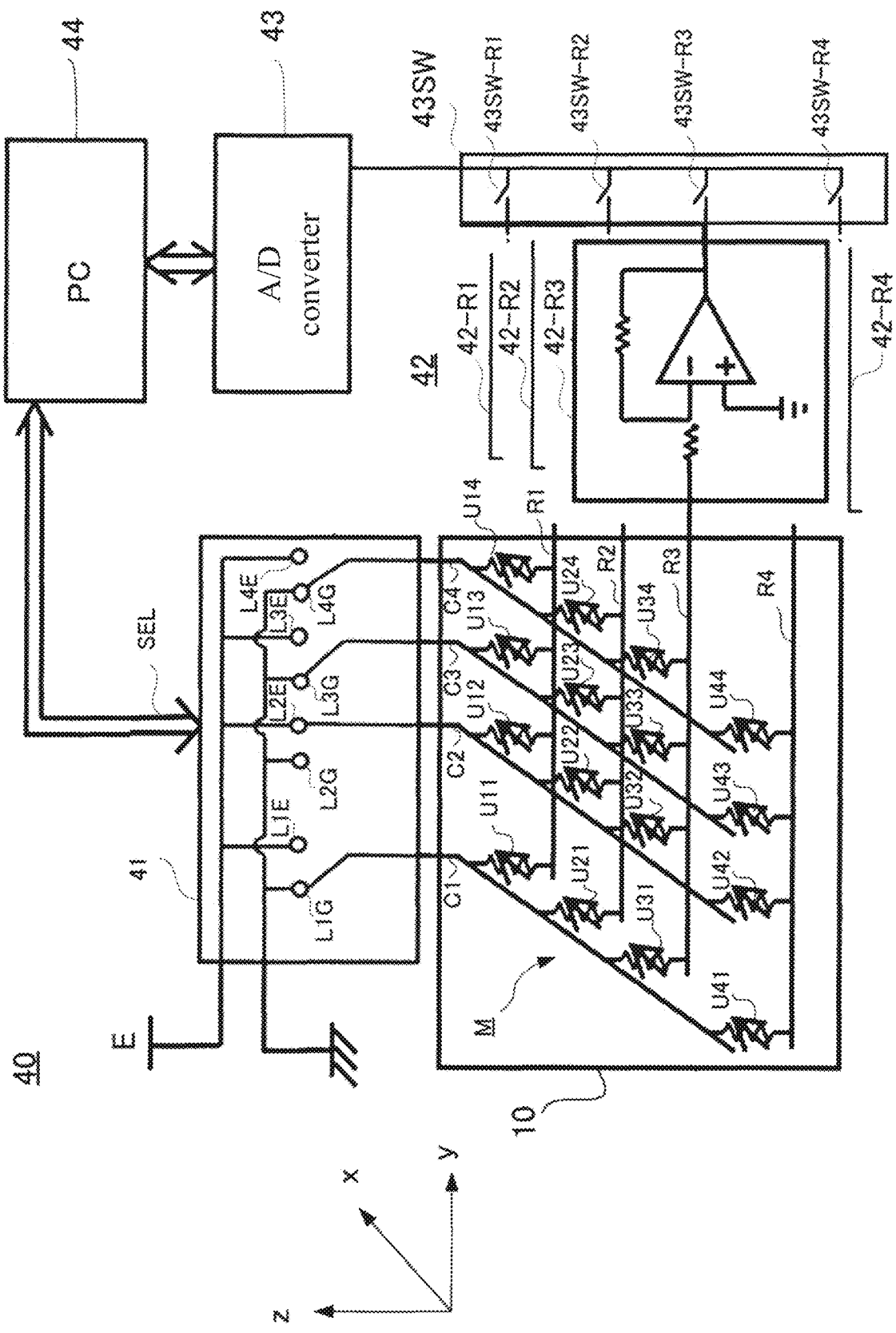
FIG. 9 shows a distribution measuring sensor system 40 using the above-described distribution measuring sensor 10 according to the present invention.

FIG. 9 shows a distribution measuring sensor system 40 using the above-described distribution measuring sensor 10 according to the present invention. In FIG. 9, parts with the same reference signs as those in FIG. 9 represent the same elements, and hence a description thereof will be omitted. In FIG. 9, a reference sign 41 denotes a relay (or a relay board) unit, and the relay unit 41 is configured to enable selecting each connecting line (a column line) Cj on the basis of an input selection signal SEL, where each upper electrode UijH of each sensor unit Uij (i=1 to 4) arranged in the same column j (j=1 to 4) of the above mentioned matrix M is connected by Cj in the column j direction in common. In the relay unit 41 are provided respective power supply side terminals (or relay contacts) L1E to L4E connected to a power supply voltage E side and respective ground side terminals L1G to L4G connected to a ground side. FIG. 9 shows an example of a state where a connecting line C2 is selected on the basis of a selection signal SEL (a state where a connecting line C1 is connected to a ground side terminal L1G, a connecting line C3 is connected to a ground side terminal LG3, a connecting line C4 is connected to a ground side terminal L4G, and the connecting line C2 is connected to a power supply side terminal L2E). A reference sign 42 designates an operation amplifier unit (an inverting amplifier circuit unit), and the operation amplifier unit 42 is constituted of respective row operation amplifiers (inverting amplifier circuits) 42-Ri (i=1 to 4) each of which has an input side connected to a connecting line (a row line) Ri (Rip to the lower electrode UijLp, Rix to the lower electrode UijLx, and Riy to the lower electrode UijLy. See FIG. 1) through which the lower electrode UijLp of the contact pressure measuring unit Uijp, the lower electrode UijLx of the x axis shear stress measuring unit Uijτx, and the lower electrode UijLy of the y axis shear stress measuring unit Uijτy of each sensor unit Uij (j=1 to 4) arranged in the same row i (i=1 to 4) of the matrix M are connected in the row i direction in common. A reference sign 43 denotes an A/D converter (an A/D conversion unit), and the converter 43 has an input side connected to the respective row operation amplifier units 42-Ri constituting the operation amplifier unit 42 through respective switches 43SW-Ri (i=1 to 4) of a switch unit 43SW. Particulars concerning the operation amplifier unit 42 and the switch unit 43SW will be described later. A reference sign 44 denotes a computer (a personal computer) PC connected to an output side of the A/D converter 43 and an input side of the relay unit 41. In the matrix M of the distribution measuring sensor 10 shown in FIG. 9, an example of Uij (rows i=1 to 4, columns j=1 to 4)

is shown, but the number of rows and the number of columns of the matrix M are not restricted to 4×4 as described above.

Next, a description will be given as to an operation of the distribution measuring sensor system 40 according to the present invention with reference to FIG. 9. As shown in FIG. 9, the selection signal SEL to select the connecting line Cj (the column j) is first output from the computer PC44 to the relay unit 41, and the connecting line Cj is selected by the relay unit 41 on the basis of the selection signal SEL (or each of the relay contacts L1E to L4E is selected). A power supply voltage E supplied to the relay unit 41 is applied to each upper electrode UijH of each sensor unit Uij (i=1 to 4) connected to the selected connecting line Cj. A voltage corresponding to a change in electrical resistance based on the contact pressure p, the x axis shear stress τx, and the y axis shear stress τy which have acted on the contact pressure measuring unit Uijp, the x axis shear stress measuring unit Uijτx, and the y axis shear stress measuring unit Uijτy of each sensor unit Uij connected to the selected connecting line Cj is output to the respective connecting lines Rip, Rix, and Riy from the respective lower electrodes UijLp, UijLx, and UijLy of the contact pressure measuring unit Uijp, the x axis shear stress measuring unit Uijτx, and the y axis shear stress measuring unit Uijτy. Each output voltage from each row operation amplifier 42-Ri unit of the operation amplifier unit 42 connected to each connecting line Ri (Rip, Rix, Riy) is output to the A/D converter 43 through each switch 43SW-Ri of the switch unit 43SW. When an output from the A/D converter 43 is output to the computer PC44, the computer PC44 sequentially repeats processing (conversion processing from the voltage to each pressure and display processing of each pressure which will be described later) to the voltage based on the contact pressure p, the x axis shear stress τx, and the y axis shear stress τy from each sensor unit Uij (i=1 to 4) corresponding to one column j selected by the selection signal SEL, and output of a selection signal to select a subsequent connecting line Cj+1 (relay control).

Figure 10:
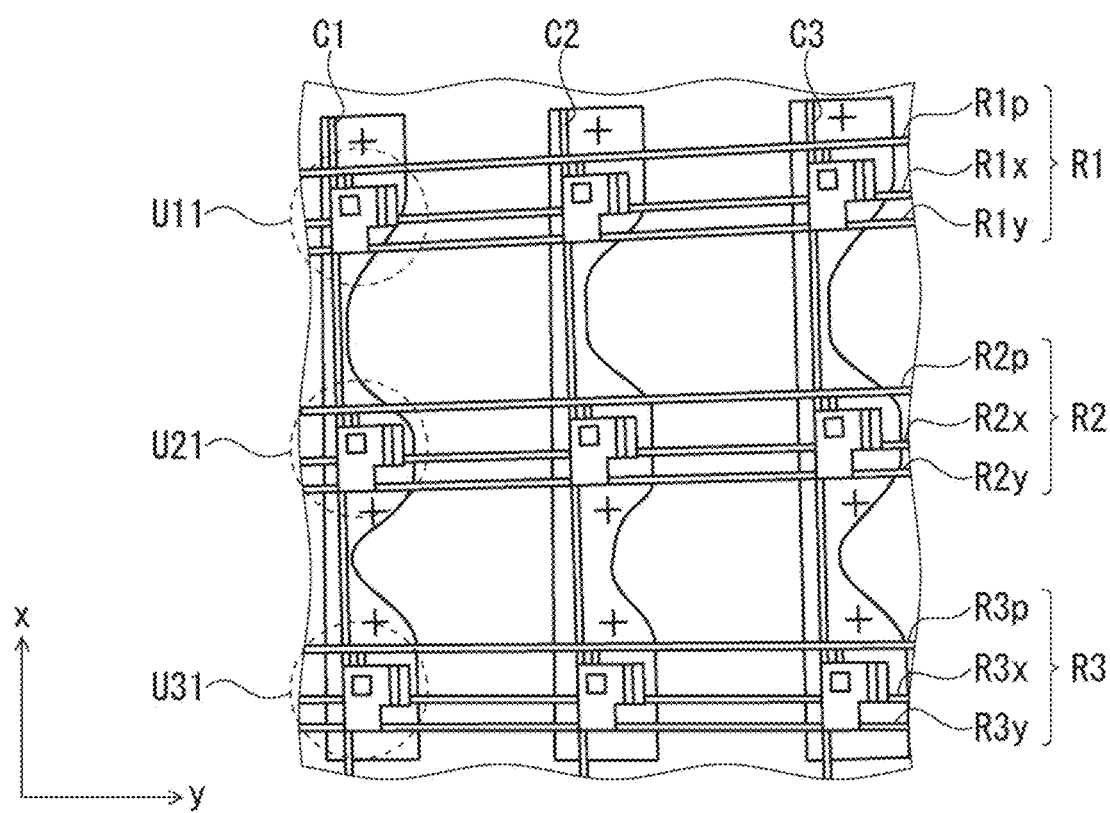
FIG. 10 shows an electrode pattern of a part of the matrix M of the distribution measuring sensor 10 in the distribution measuring sensor system 40 shown in FIG. 9.

FIG. 10 shows an electrode pattern of a part of the matrix M of the distribution measuring sensor 10 in the distribution measuring sensor system 40 shown in FIG. 9. In FIG. 10, parts with the same reference signs as those in FIG. 1 represent the same elements, and hence a description will be omitted. FIG. 10 corresponds to a view obtained by rotating a view, which shows a state where the respective electrode patterns of the upper electrodes UijH and the lower electrodes UijL are overlapped vertically shown in FIG. 8(B), 90° in a counterclockwise direction. In FIG. 10, some of the sensor units Uij (i=1 to 3, j=1 to 3) are shown. The upper electrodes U11H, U21H, and U31H (not shown) of the respective sensor units U11, U21, and U31 in the first column are connected in the first column direction (the x axis direction) in common through the connecting line C1. Since the same applies to the other sensor units Ui2 and Ui3 (i=1 to 3) in the second column and the third column, a description thereof will be omitted. The respective lower electrodes U1jL (j=1 to 3) of the sensor units U11, U12, and U13 are connected in the first row direction (the y axis direction) in common through the connecting line R1. More specifically, the respective lower electrodes U1jLx (j=1 to 3) are connected in the first row direction in common through the connecting line R1x, the respective lower electrodes U1jLy (j=1 to 3) are connected in the first row direction in common through the connecting line R1y, and the respective lower electrodes U1jLp (j=1 to 3) are connected in the first row direction in common through the connecting line Rip.

Since the same applies to the other sensor units U2j and U3j (j=1 to 3) the second row and the third row, a description thereof will be omitted.

Figure 11:
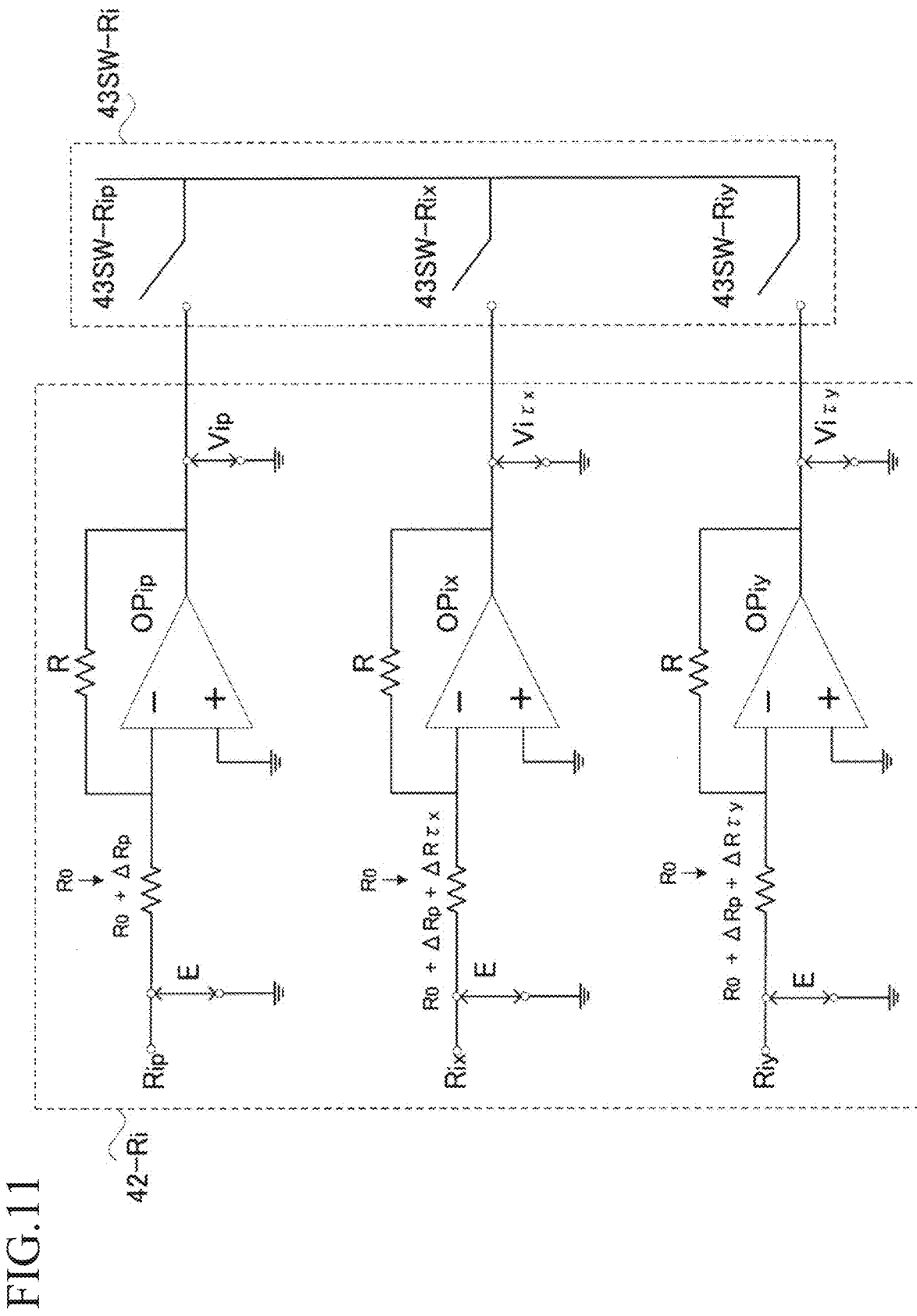
FIG. 11 shows an enlarged view of the row operation amplifier unit 42-Ri of the operation amplifier unit 42 and the switch 43SW-Ri of the switch unit 43SW connected to the output voltage side of the row amplifier unit 42-Ri shown in FIG. 9.

FIG. 11 shows an enlarged view of the row operation amplifier unit 42-Ri of the operation amplifier unit 42 and the switch 43SW-Ri of the switch unit 43SW connected to the output voltage side of the row amplifier unit 42-Ri shown in FIG. 9. In FIG. 11, parts with the same reference signs as those in FIG. 9 represent the same elements, and hence a description thereof will be omitted. As shown in FIG. 11, the row operation amplifier unit 42-Ri is constituted of an operation amplifier OPip connected to the connecting line Rip from the lower electrode UijLp of the contact pressure measuring unit Uijp, an operation amplifier OPix connected to the connecting line Rix from the lower electrode UijLx of the x axis shear stress measuring unit Uijτx, and an operation amplifier OPiy connected to the connecting line Riy from the lower electrode UijLy of the y axis shear stress measuring unit Uijτy. In FIG. 11, a reference sign R0 denotes an interelectrode resistance between the upper electrode UijH and each lower electrode UijLx, or UijLy in a no-load state of the contact pressure p, the x axis shear stress τx, and the y axis shear stress τy, and three interelectrode resistances are designed to become equal in the no-load state (=R0. For example, 10 to 100 kΩ) and serve as input side resistances of the operation amplifiers OPip, Opix, and OPiy. A reference sign R denotes a feedback resistance (e.g., 1 to 10 kΩ), and E designates a power supply voltage (e.g., 5 V) applied to the sensor unit Uij and serves as an input voltage of the operation amplifiers OPip, Opix, and OPiy. Reference signs Vip, Viτx, and Viτy represent output voltages of the operation amplifiers OPip, OPix, and OPiy, respectively. A reference sign 43SW-Rip denotes a switch in the switch 43SW-Ri connected to the output side of the operation amplifier OPip, 43SW-Rix denotes a switch in the switch 43SW-Ri connected to the output side of the operation amplifier OPix, and 43SW-Riy denotes a switch in the switch 43SW-Ri connected to the output side of the operation amplifier OPiy.

Here, in case of loading of the contact pressure p to the sensor unit Uij, the interelectrode resistance between the upper electrode UijH and the lower electrode UijLp changes by ΔRp, and the input side resistance R0 of the operation amplifier OPip becomes R0+ΔRp. An output voltage Vip (which will be simply abbreviated as "Vp" in the following expression) is represented by the following Expression 1.

[Numerical formula 3]

$$V_p = -\frac{R}{(R_0 + \Delta R_p)} E \quad (1)$$

In case of loading of the shear stress TX to the sensor unit Uij, the interelectrode resistance between the upper electrode UijH and the lower electrode UijLx changes by ΔRτx, and the input side resistance R0 of the operation amplifier OPix becomes R0+ΔRP+ΔRτx. An output voltage Viτx (which will be simply abbreviated as "Vτx" in the following expression) is represented by the following Expression 2.

[Numerical formula 4]

$$V_{\tau x} = -\frac{R}{(R_0 + \Delta R_p + \Delta R_{\tau x})}E \quad (2)$$

In case of loading of the shear stress τy to the sensor unit Uij, the interelectrode resistance between the upper electrode UijH and each lower electrode UijLy changes by ΔRτy, and the input side resistance R0 of the operation amplifier OPiy becomes R0+ΔRp+ΔRτy. An output voltage Viτy (which will be simply abbreviated as "Vτy" in the following expression) is represented by the following Expression 3.

[Numerical formula 5]

$$V_{\tau y} = -\frac{R}{(R_0 + \Delta R_p + \Delta R_{\tau y})}E \quad (3)$$

The above-described respective output voltages Vip, Viτx, and Viτy are output to the A/D converter 43 side when the respective switches 43SW-Rip, 43SW-Rix, and 43SW-Riy are sequentially opened or closed on the basis of control from the computer PC44. Particulars will be described later. It is to be noted that Expression 2 and Expression 3 can be unified and represented like Expression 4, In Expression 4, ΔRτ is a variation of the interelectrode resistance in which variations ΔRτx and ΔRτy of the interelectrode resistance are unified, and Vτ is an output voltage in which respective output voltages Viτx and Viτy of the operation amplifiers OPix and OPiy are unified and a suffix i is omitted as described above.

[Numerical formula 6]

$$V_{\tau} = -\frac{R}{(R_0 + \Delta R_p + \Delta R_{\tau})}E \quad (4)$$

Figure 12:
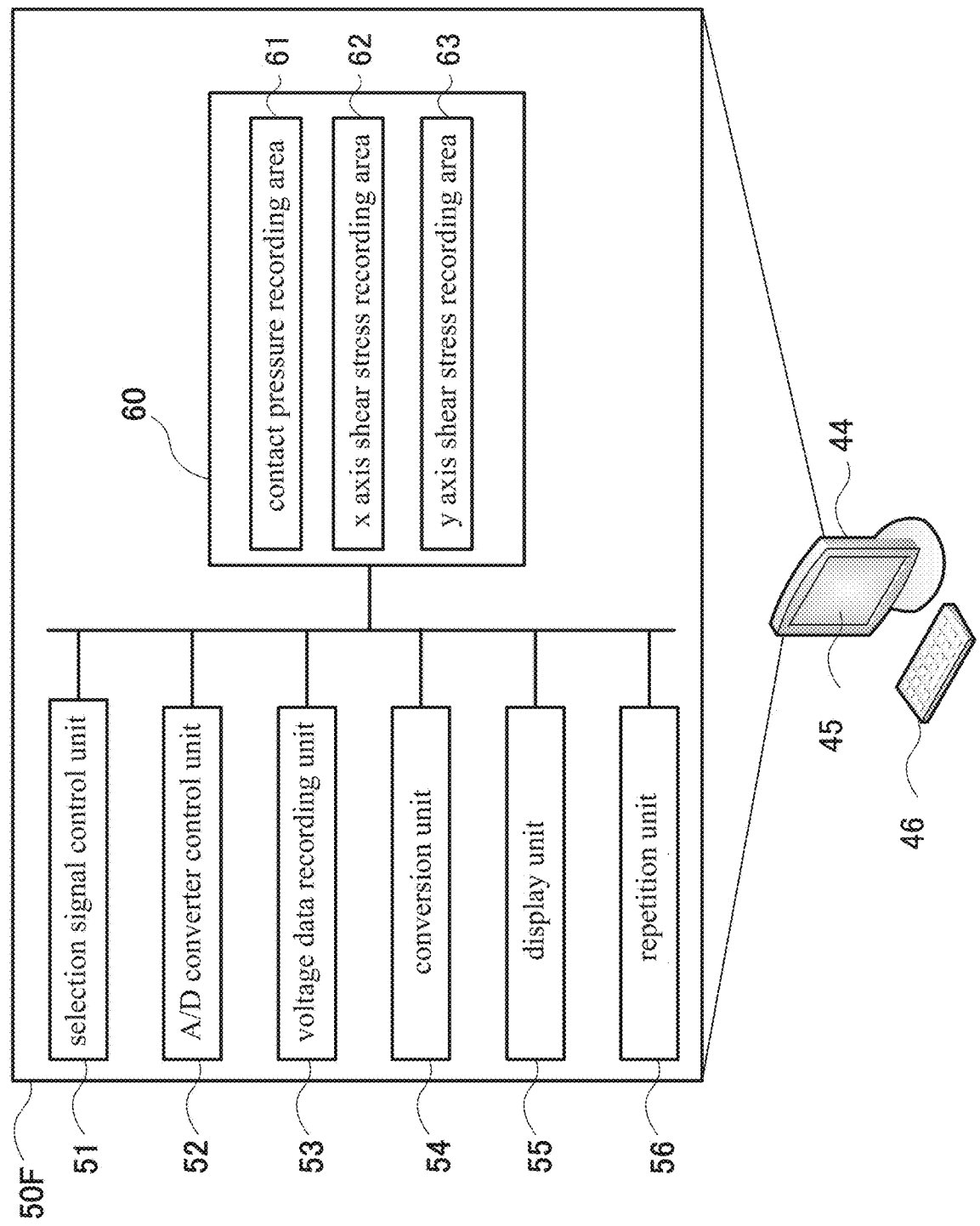
FIG. 12 shows a block 50F of functions and others showing functions of the computer PC44 (functions of programs or software) and a recording region (a memory, a hard disk, or the like) in the distribution measuring sensor system 40 according to the present invention.

FIG. 12 shows a block 50F of functions and others showing functions of the computer PC44 (functions of programs or software) and a recording region (a memory, a hard disk, or the like) in the distribution measuring sensor system 40 according to the present invention. In FIG. 12, a reference sign 45 denotes a display (an output display unit) which displays a processing result or the like of the computer PC44, and 46 designates an input device such as a keyboard, a mouse, and the like to input instructions, data, and others to the computer PC44. A description will be given below on a program which operates on the computer PC44 with reference to the block 50F of functions and others shown in FIG. 12 and the distribution measuring sensor system 40 shown in FIG. 9. In the following description, the matrix M shown in FIG. 1 or FIG. 9 is constituted of m rows×n columns.

A selection signal control unit (selection signal controlling means) 51 shown in the block 50F of functions and others in FIG. 12 outputs the selection signal SEL to select a designated column j (j=1 to n) in the matrix M to the relay unit 41.

As described above, the A/D converter 43 has the input side connected to the respective row operation amplifier units 42-Ri constituting the operation amplifier unit 42 through the respective switches 43SW-Ri (i=1 to m) of the switch unit 43SW (see FIG. 11). An A/D converter control unit (A/D conversion unit controlling means) 52 shown in the block 50 of functions and others in FIG. 12 sequentially inputs output voltages Vip, Viτx, and Viτy from each row operation amplifier unit 42-Ri of the operation amplifier unit 42 based on the contact pressure p, the x axis shear stress τx, and the y axis shear stress τy obtained from each sensor unit Uij (i=1 to m) corresponding to one column j by sequentially selecting each switch 43SW-Ri of the A/D converter 43 in relation to the column j selected by the selection signal SEL output from the selection signal control unit 51. Specifically, the output voltages V1p, V1τx, and V1τy from the row operation amplifier unit 42-R1 based on the contact pressure p, the x axis shear stress τx, and the y axis shear stress τy obtained from the sensor unit U1j in the selected column j and the first row are input to the A/D converter 43 by selecting the switch 43SW-R1. Then, the output voltages V2p, V2τx, and V2τy from the row operation amplifier unit 42-R2 based on the contact pressure p, the x axis shear stress τx, and the y axis shear stress τy obtained from the sensor unit U2j in the column j and the second row are input to the A/D converter 43 by selecting the switch 43SW-R2. The above-described processing is continued, and the output voltages Vmp, Vmτx, and Vmτy from the row operation amplifier unit 42-Rm based on the contact pressure p, the x axis shear stress τx, and the y axis shear stress τy obtained from the sensor unit Umj in the column j and the m-th row are input to the A/D converter 43 by selecting the switch 43SW-Rm. Thus, in relation to the column j selected by SEL, the output voltages Vip, Viτx, and Viτy from each row operation amplifier unit 42-Ri of the operation amplifier unit 42 based on the contact pressure p, the x axis shear stress τx, and the y axis shear stress τy obtained from each sensor unit Uij (i=1 to m) corresponding to one row j are sequentially input to the A/D converter 43 by sequentially selecting each switch 43SW-Ri of the A/D converter 43.

A voltage data recording unit (voltage data recording means) 53 shown in the block 50F of functions and others in FIG. 12 records voltage data Vpd, Vτxd, and Vτyd based on the contact pressure p, the x axis shear stress τx, and the y axis shear stress τy from each sensor unit Uij, which have been input to the A/D converter 43 by the A/D converter control unit 52 and subjected to A/D conversion by the A/D converter 43, in a contact pressure recording area (a contact pressure recording region) 61, an x axis shear stress recording area (an x axis shear stress recording region) 62, and a y axis shear stress recording area (a y axis shear stress recording region) 63 for each sensor unit Uij. Specifically, as regards the column j selected by the selection signal SEL, the voltage data Vpd, Vτxd, and Vτyd from each sensor unit Uij (i=1 to m), which have been sequentially obtained from each sensor unit Uij (i=1 to m) corresponding to one column, sequentially input to the A/D converter 43 by sequentially selecting each switch 43SW-Ri (i=1 to m), and subjected to the A/D conversion by the A/D converter 43 are recorded in the contract pressure recording area 61, the x axis shear stress recording area 62, and they axis shear stress recording area 63 for each sensor unit Uij (i=1 to m). A later-described repetition unit 56 selects a subsequent column j+1, and the voltage data recording unit 53 performs the same processing as that described above in relation to the column j+1, whereby the respective A/D-converted voltage data Vpd, Vτxd, and Vτyd (each corresponding to i=1 to m and j=1 to n) are recorded in the contact pressure recording area 61, the x axis shear stress recording area 62, and the y axis shear stress recording area 63, which are provided in m×n sets, corresponding to the sensor unit Uij (i=1 to in, j=1 to n).

A conversion unit (converting means) 54 shown in the block 50F of functions and others in FIG. 12 converts the respective voltage data Vpd, Vτxd, and Vτyd recorded in the contact pressure recording area 61, the x axis shear stress recording area 62, and the y axis shear stress recording area 63 for each sensor unit Uij by the voltage data recording unit 53 into the contact pressure p, the x axis shear stress τx, and the y axis shear stress τy acting on each sensor unit Uij on the basis of a relationship according to predetermined measurement principles between the contact pressure p, the x axis shear stress τx, and the y axis shear stress τy acting on the sensor unit Uij and the respective output voltages Vip, Viτtx, and Viτy from the respective operation amplifiers OPip, OPix, and OPiy connected to the respective lower electrodes UijLp, UijLx, and UijLy.

The predetermined measurement principles will be described below. First, a description will be given on a predetermined measurement principle (1) between the contact pressure p acting on the sensor unit Uij and each output voltage Vip from each operation amplifier OPip connected to the lower electrode UijLp in the conversion unit 54. The above-described Expression 1 can be represented like the following Expression 5.

[Numerical formula 7]

$$\frac{V_p}{E} = -\frac{R}{(R_0 + \Delta R_p)} \quad (5)$$

As represented by Expression 5, the output voltage Vp based on the contact pressure p can be represented by using a resistance variation ($\Delta Rp$) based on the contact pressure p alone. Thus, the predetermined measurement principle 1) is a measurement principle that obtaining a relationship between the contact pressure p and a left-hand side of Expression 5 (Vp/E) corresponding thereto by an experiment in advance enables obtaining (converting) the contact pressure p from the relationship thereafter by measuring the output voltage Vp. As described above, when the shear stress τx in the x axis direction and the shear stress τy in the y axis direction act on the contact pressure measuring unit Uijp, in the overlapping region in the contact pressure measuring unit Uijp, a mutual positional displacement in the x and y axis directions occurs, but a deformation in the z axis direction does not occur. Thus, measuring the output voltage Vp enables detecting the contact pressure p in the z axis direction without being interfered with the shear stress τx in the x axis direction and the shear stress τy in the y axis direction.

A description will now be given as to a predetermined measurement principle (2) between the x axis shear stress τx and the y axis shear stress τy acting on the sensor unit Uij and the respective output voltages Viτx and Viτy from the respective operation amplifiers OPix and OPiy connected to the respective lower electrodes UijLx and UijLy in the conversion unit 54. For the purpose of illustration, as described above, the x axis shear stress τx and the y axis shear stress τy are unified as a shear stress τ, the output voltages Viτtx and Viτy are unified as Vτ, and the interelectrode resistance variations ΔRτx and ΔRτy are unified as ΔRτ. The following Expression 6 can be obtained from Expression 1 and Expression 4.

[Numerical formula 8]

$$\left(\frac{1}{V_\tau} - \frac{1}{V_p}\right) \times E = -\frac{\Delta R_\tau}{R} \quad (6)$$

As represented by Expression 6, the output voltage Vp based on the contact pressure and the output voltage Vτ based on the shear stress can be represented by the resistance variation ΔRτ based on the shear stress alone. That is, a resistance variation due to the contact pressure p in the x axis and y axis shear stress measuring units Uijτx and Uijτy can be excluded, and the shear stress τ (τx, τy) alone can be detected. Thus, the predetermined measurement principle (2) is a measurement principle that obtaining a relationship between the shear stress τ (τx, τy) and a left-hand side {(1/Vτ)−(1/Vp)}×E of Expression 6 corresponding thereto by an experiment in advance enables obtaining (converting) the shear stress τ from the relationship thereafter by measuring the output voltages Vτ and Vp. As described above, the shear stress measuring unit Uijτx can detect the shear stress τx in the x axis direction alone without being interfered with the shear stress τy in the y axis direction. The shear stress measuring unit Uijτy can detect the shear stress τy in the y axis direction without being interfered with the shear stress τx in the x axis direction. Thus, on the basis of the measured shear stresses τx and τy, magnitude and an acting direction of the shear stress τ can be discriminated. It is to be noted that sensitivity to the contact pressure p and the shear stress τ to be measured can be adjusted by adjusting the feedback resistance R.

A display unit (displaying means) 55 in the block 50F of functions and others in FIG. 12 displays the contact pressure p, the x axis shear stress τx, and the y axis shear stress τy acting on each sensor unit Uij which have been converted by the conversion unit 54 in a predetermined display format in a display 45 of the computer PC44. The predetermined display formation will be described later.

The repetition unit (repeating means) 56 shown in the block 50F of functions and others in FIG. 12 designates a column j+1 following the column j selected by the selection signal SEL output from the selection signal control unit 51 to repeat the processing of the selection signal control unit 51 to the display unit 55.

The description has been given as to the functions (the functions of the programs and the software) of the computer PC44 in the distribution measuring sensor system 40. Aside from this, it is also possible to adopt a configuration in which the computer PC44 side supplies a start signal START to start selection of the column j (j=1 to n) in the matrix M to the relay unit 41 side and the relay unit 41 side executes repetition of selection of the subsequent column j (C1, C2, C3, C4, C1, C2, . . . ) on the basis of a predetermined synchronization signal with the use of hardware. The A/D converter control unit 52 and the voltage data recording unit 53 on the PC44 side perform the A/D conversion to a supplied output voltage on the basis of the synchronization signal and record voltage data in the contact pressure recording area 61, the x axis shear stress recording area 62, and the y axis shear stress recording area 63. After elapse of a desired time, the computer PC44 side may supply an end signal STOP to end selection of the column j (j=1 to n) in the matrix M to the relay unit 41 side so that the relay unit 41 side ends the selection of the column j. Some of the functions of the computer PC44 (the functions of the programs and the software) shown in the block 50F of functions and others in FIG. 12 can be also realized by hardware as described above.

As described above, the distribution measuring sensor 10 has the shape in which the upper electrodes UijH and the lower electrodes UijL having the pressure sensitive materials 20p, 20x, 20y, 20, and the like interposed therebetween are arranged in the form of the matrix M (a plurality of vertically long (columns) and a plurality of horizontally long (rows)), and many measurement points can be arranged at intersection points (the elements of the matrix M) of the upper and lower electrodes by coupling many sensor units Uij (the measurement points) through the connecting lines Ci and Ri. With this matrix-shaped configuration, information of the contact pressure and the shear stresses is not obtained by scanning the measurement points one by one, but information of each sensor unit Uij (the intersection point) can be obtained by sequentially selecting each switch SW-Ri to sequentially select each row (i=1 to as described above in a state where one column j in the matrix M is selected. Further, a subsequent column j+1 can be selected by the repetition unit 56 (which will be described later), and matrix type scanning to obtain information of the sensor unit Uij+1 can be carried out like the column j. Consequently, even if many sensor units Uij are integrated to grasp distributions of the contact pressure and the shear stress, a wiring region can be greatly reduced, a design can be simplified, an increase in manufacturing costs can be suppressed, and a considerable effect, i.e., a groundbreaking advance of spatial resolution enhancement of the contact pressure/and the shear stress distribution can be exerted.

Figure 13:
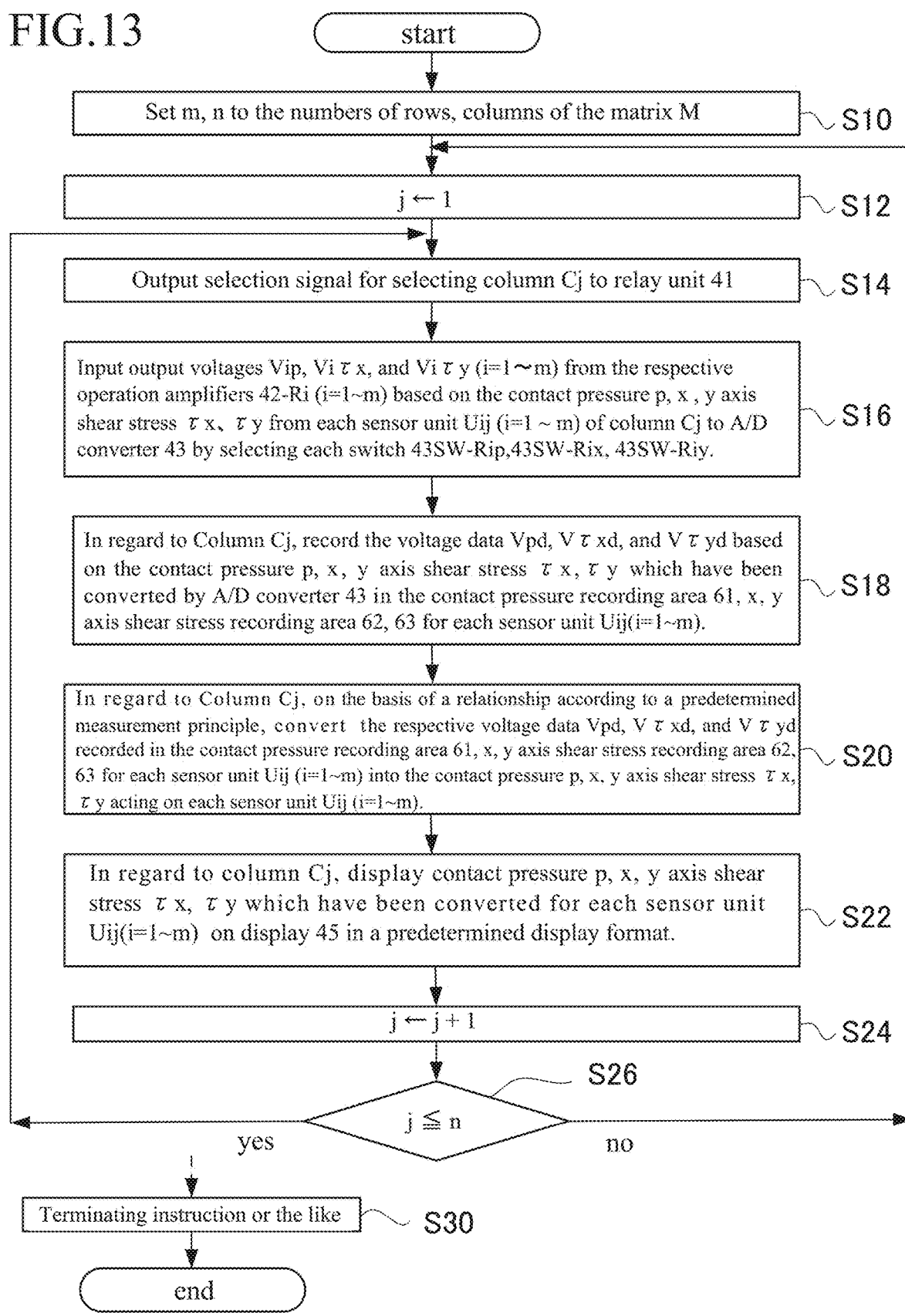
FIG. 13 shows a flow of processing of a distribution measuring program to operate the computer PC44 in the distribution measuring sensor system 40 according to the present invention in the form of a flowchart.

FIG. 13 shows a flow of processing of a distribution measuring program to operate the computer PC44 in the distribution measuring sensor system 40 according to the present invention in the form of a flowchart. As shown in FIG. 13, the number of rows in the matrix M is set to a variable m, the number of columns is set to n (a step S10), and 1 is set to a variable j which represents the number of columns (a step S12).

Then, the selection signal SEL to select a designated column Cj in the matrix M is output to the relay unit 41 (a selection signal controlling step. A step S14). Subsequently, in relation to the column Cj selected by the selection signal SEL output at the selection signal controlling step (the step S14), the respective output voltages Vip, Viτx, and Viτy from the respective operation amplifiers OPip, OPix, and OPiy of the row operation amplifier unit 42-Ri based on the contact pressure p, the x axis shear stress τx, and the y axis shear stress τy from each sensor unit Uij (i=1 to m) corresponding to one column are sequentially input to the A/D converter 43 by selecting each switch 43SW-Ri of the A/D converter 43 (an A/D converter (A/D conversion unit) controlling step. A step S16).

The voltage data Vpd, Vτxd, and Vτyd based on the contact pressure p, the x axis shear stress τx, and the y axis shear stress τy from each sensor unit Uij which have been input to the A/D converter 43 and subjected to the A/D conversion by the A/D converter 43 at the A/D converter controlling step (the step S16) are recorded in the contact pressure recording area 61, the x axis shear stress recording area 62, and the y axis shear stress recording area 63 for each sensor unit Uij (a voltage data recording step. A step S18).

On the basis of a relationship according to the predetermined measurement principles (the measurement principles (1) and (2)) between the contact pressure p, the x axis shear stress τx, and the y axis shear stress τy acting on the sensor unit Uij and the respective output voltages Vip, Viτx, and Viτy from the respective operation amplifiers OPip, OPix, and OPiy connected to the respective lower electrodes UijLP, UijLx, and UijLy, the respective voltage data Vpd, Vτxd, and Vτyd recorded in the contact pressure recording area 61, the x axis shear stress recording area 62, and the y axis shear stress recording area 63 for each sensor unit Uij at the voltage data recording step (the step S18) are converted into the contact pressure p, the x axis shear stress τx, and the y axis shear stress τy acting on each sensor unit Uij (a converting step. A step S20).

The contact pressure p, the x axis shear stress τx, and the y axis shear stress τy acting on each sensor unit Uij converted at the converting step (the step S20) are displayed in the display 45 of the computer PC44 in a predetermined display format (a displaying step. A step S22).

A column j+1 following the column j selected by the selection signal SEL output at the selection signal controlling step (the step S14) is designated (j is incremented to J+1. A step S24), and the processing from the selection signal controlling step (the step 14) to the display step (the step S22) is repeated when new j is equal to or less than the number of columns n in the matrix M (in case of "yes" at the step S26), or the processing from the step 12 to the same is repeated when new j is larger than n (in case of "no" at the step S26) (a repeating step).

When a terminating instruction or the like is input from the input device 46 such as a keyboard of the computer PC44 (a step S30), the processing of the distribution measuring program is terminated.

Experiment Method

Figure 14:
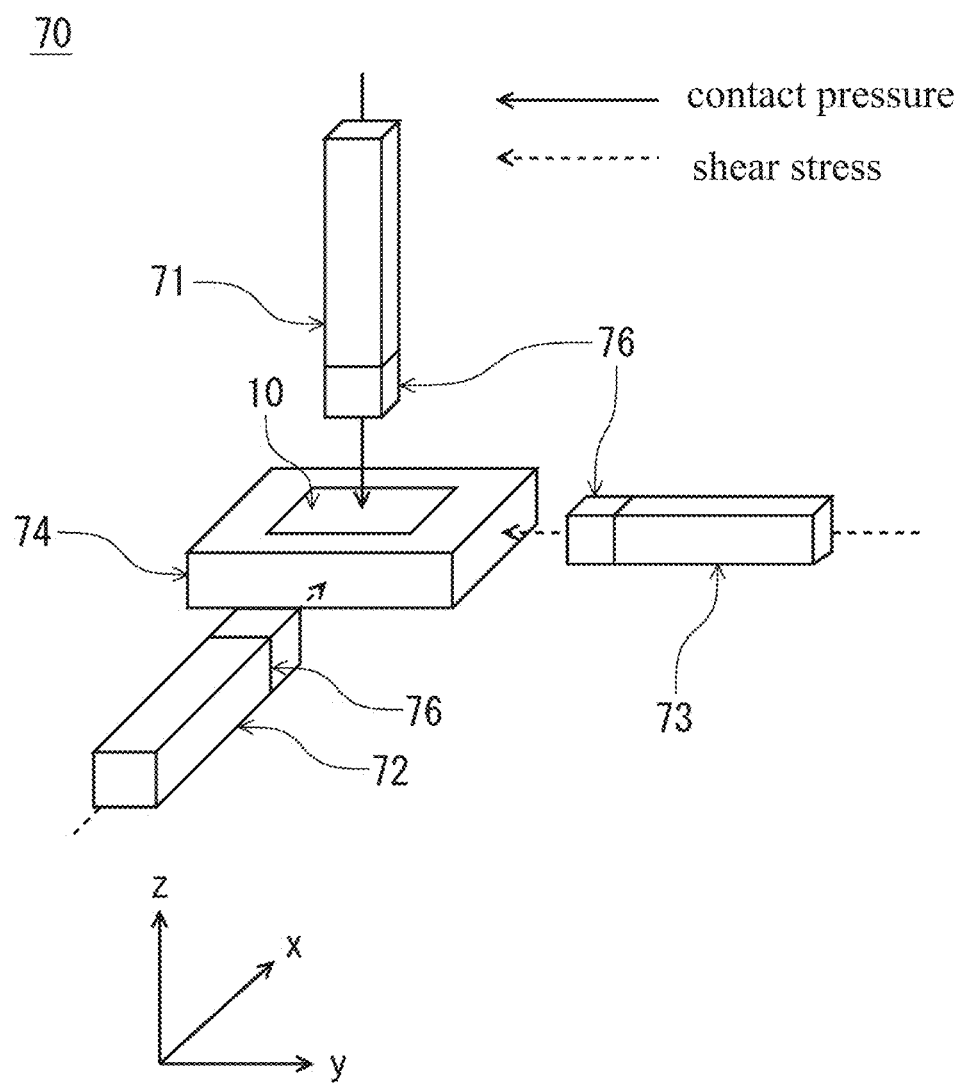
FIG. 14 is a schematic view showing functions of a calibration device 70 fabricated to conduct calibration experiments.

As described above, according to the distribution measuring sensor system 40 of the present invention, simultaneous measurement of the contact pressure p and the x axis shear stress τx or the y axis shear stress τy of the sensor unit Uij can be performed. Here, to consider effectiveness of the simultaneous measurement, a calibration experiment of the contact pressure p, and the x axis shear stress τx and the y axis shear stress τy of the fabricated sensor unit Uij was conducted. FIG. 14 is a schematic view showing functions of a calibration device 70 fabricated to conduct calibration experiments. As shown in FIG. 14, the distribution measuring sensor 10 is installed on an X-Y stage 74 (other devices of the distribution measuring sensor system 40 are not shown), and the calibration device 70 is configured in such a manner that an arbitrary contact pressure p and sheer stress τx and τy act on the distribution measuring sensor 10 on the X-Y stage 74 by using an actuator 71 (one) for the contact pressure p and actuators 72 (for the x axis) and 73 (for the y axis) (two) for the shear stresses τ. Compression type load cells 76 are installed at tips of the actuators 71, 72, and 73, respectively.

The above-described measurement principle (1) is a measurement principle that obtaining a relationship between the contact pressure p and a left-hand side (Vp/E) of Expression 5 corresponding thereto by an experiment in advance enables obtaining (converting) the contact pressure p from the relationship thereafter by measuring the output voltage Vp. Experiment 1 is an experiment to confirm this measurement principle (1) and, specifically, an experiment (Experiment 1) to load the sensor unit Uij with the contact pressure p of up to 100 kPa was conducted by using the calibration device 70.

The above-described measurement principle (2) is a measurement principle that obtaining a relationship between the shear stress τ (τx, τy) and a left-hand side $\{(1/\tau)-(1/Vp)\}\times E$ of Expression 6 corresponding thereto by an experiment in advance enables obtaining (converting) the shear stress τ from the relationship by measuring each of the output voltages Vτ and Vp. Experiment 2 is an experiment to confirm this measurement principle (2) and to confirm that the contact pressure p and the x-axis shear stress τx (the y axis shear stress τy) of the sensor unit Uij can be simultaneously measured. Specifically, an experiment (Experiment 2) to load the sensor unit Uij with the x axis shear stress τx of −40 to 40 kPa was conducted with the use of the calibration device 70 in a state where the contact pressures p of 50 kPa and 100 kPa were acting. It is to be noted that an experiment in a state where the y axis shear stress τy is acting is omitted in this specification.

As described above, one of the objects of the present invention is to provide the distribution measuring sensor system or the like with a high spatial resolution which is applicable to the measurement of the contact pressure and the shear stress acting on an interface between a living body and an object. Thus, an experiment (Experiment 3) to bond the distribution measuring sensor 10 to a cylindrical container (e.g., a bottle) and measure changes in contact pressure p and in x axis shear stress τx or y axis shear stress τy when the bottle is lifted up with human fingers was conducted. That is, it is preferable for a plane constituted of the x axis and the y axis to be an interface between a living body and a solid substance. In Experiment 3, the human fingers are taken as a living body and the container is taken as a solid substance, but this is an example, and the living body and the solid substance are not restricted to the human fingers and the container, respectively.

Result and Consideration of Experiment 1.

Figure 15:
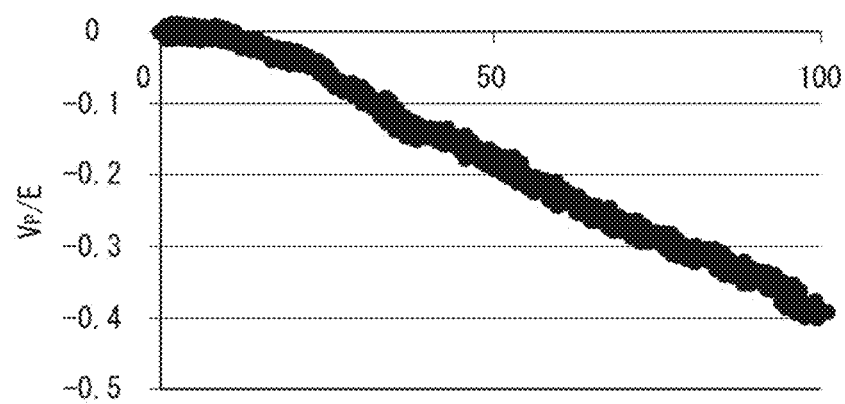
FIG. 15 is a graph showing output voltage changes (Vp/E) to the contact pressure p as a result of Experiment 1.

FIG. 15 is a graph showing output voltage changes (Vp/E) to the contact pressure p as a result of Experiment 1. In FIG. 15, an horizontal axis represents the contact pressure p (kPa) applied to (caused to act on) the sensor unit Uij (one measurement point) of the distributing measuring sensor 10, and an vertical axis represents a left-hand side (Vp/E) of Expression 5, i.e., each value based on an output voltage Vp (which is precisely Vip) from the operation amplifier OPip shown in FIG. 11. As shown in FIG. 15, it can be understood that substantially linear output voltage changes (Vp/E) to the contact pressure p which has been caused to act can be observed. Thus, based on the graph shown in FIG. 15, measuring the output voltage Vp enables obtaining the contact pressure p which has been caused to act. In Expression 5, a right-hand side=−R/R0 and is not 0 when the contact pressure p=0, i.e., when the resistance variation ΔRp=0, but it seems that 0 is attained in FIG. 15. However, when the interelectrode resistance R0 at the time of no load is sufficiently larger than the feedback resistance R, the right-hand side becomes 0.

Result and Consideration of Experiment 2.

Figure 16:
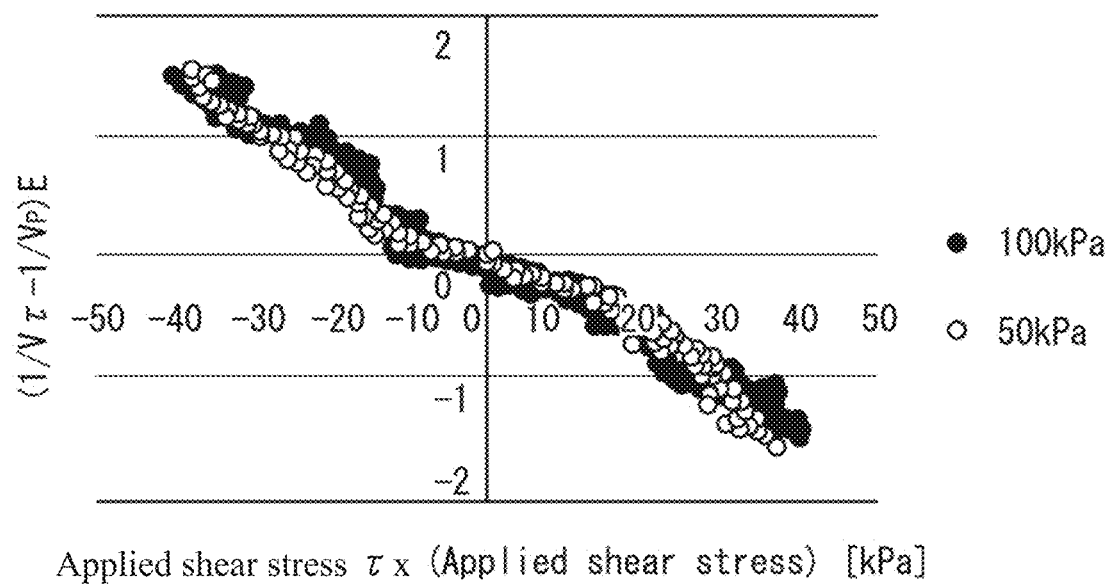
FIG. 16 is a graph showing output voltage changes [(1/Vτ)−(1/Vp)]×E] to the shear stress τx which is a result of Experiment 2.

FIG. 16 is a graph showing output voltage changes [(1/Vτ)−(1/Vp)]×E] to the shear stress τx which is a result of Experiment 2. In FIG. 16, an horizontal axis represents the shear stress τx (kPa) applied (caused to act on) the sensor unit Uij (one measurement point) of the distribution measuring sensor 10, and an vertical axis is a value based on a left-hand side [{1/Vτ}−(1/Vp)]×E] of Expression 6, i.e., an output voltage Vp (which is precisely Vip) from the operation amplifier OPip and an output voltage Vτ (which is precisely a voltage based on Vix and Viy) from the operation amplifier OPix or OPiy. Although the horizontal axis represents the shear stress τx in FIG. 16, since the same measurement results can be obtained in regard to the shear stress τy, the shear stress τx on the horizontal axis represents τ in which the shear stresses τx and τy are unified. In FIG. 16 (an original drawing), each output voltage change to the shear stress τx in a state where the contact pressure p of 50 kPa is caused to act is represented by a red circle, and each output voltage change to the shear stress τx in a state where the contact pressure of 100 kPa is caused to act is represented by a blue circle. In FIG. 16 (black and white), each red circle is shown like a thick circle, and each blue circle is shown like a thin circle. As shown in FIG. 16, it can be understood that substantially linear output voltage changes [{(1/Vτ)−(1/Vp)}×E] to the shear stress τx caused to act can be observed. Thus, on the basis of the graph shown in FIG. 16, measuring the output voltages Vp and Vτx enables obtaining the shear stress τx which has been caused to act. Further, since a relationship (a linear shape) between the shear stress τx and the output voltage changes [{(1/Vτ)−(1/Vp)}×E] do not change even if the contact pressure p is changed to 50 kPa and 100 kPa, it can be understood that the contact pressure p and the shear stress τx can be independently measured even if composite loading is performed. That is, the effectiveness of the simultaneous measurement of the contact pressure p and the x axis shear stress τx (and τy) of the sensor unit Uij has been proven.

Result and Consideration of Experiment 3

Figure 17:
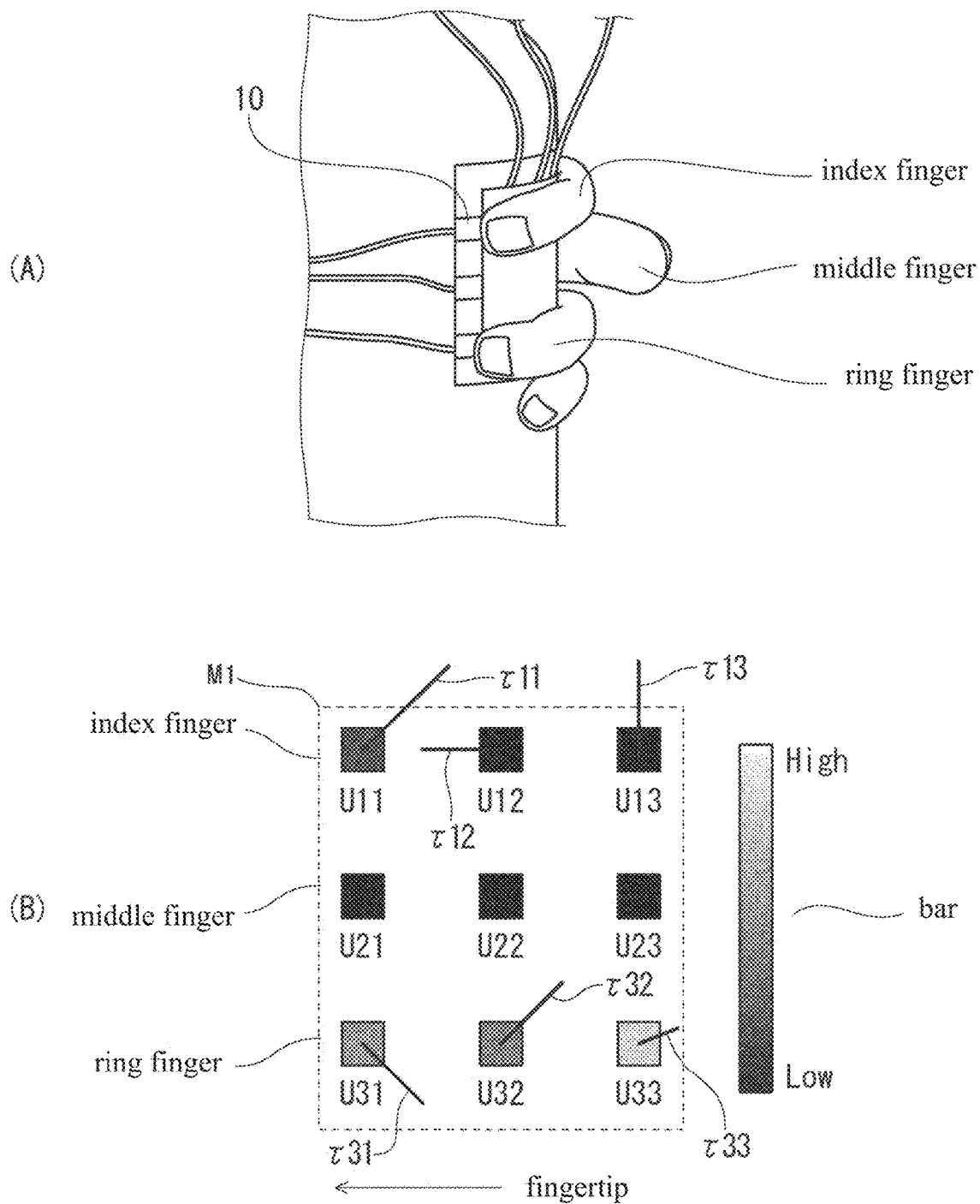
FIG. 17 show a distribution of the contact pressure p and the shear stress τ (τx+τy) when the distribution measuring sensor 10 has bonded to a cylindrical container (a bottle or the like) and lifted up with human fingers, which is a result of Experiment 3.

FIG. 17 show a distribution of the contact pressure p and the shear stress τ (τx+τy) when the distribution measuring sensor 10 has bonded to a cylindrical container (a bottle or the like) and lifted up with human fingers, which is a result of Experiment 3. FIG. 17(A) is a photograph when the distribution measuring sensor 10 (a matrix M1 of 3 rows×3 columns) bonded to the cylindrical container is lifted up with human fingers. All other devices in the distributing measuring sensor system 40 are omitted in the photograph. As shown in FIG. 17(A), the distribution measuring sensor 10 is held with an index finger and a ring finger (which correspond to a first row and a third row of the matrix M1, respectively), and a middle finger is taken off (a second row of the matrix MI is not touched).

FIG. 17B shows an image displayed in the display 45 by the display unit 55 in a state of FIG. 17(A). A description will be given below on a predetermined display format in the display unit 55. Each sensor unit Uij (i=1 to 3, j=1 to 3) in the matrix M1 of the distribution measuring sensor 10 is represented as a square at a position of a corresponding element as shown in FIG. 17(B). In FIG. 17(B), magnitude of the contract pressure p acting on the container is represented by a color of each square (the color is in the original drawing. The same applies hereafter). As shown on a right-side bar in FIG. 17(B), the magnitude of the contact pressure p is represented by a color of a waveform on a red side as it intensifies (High), and the same is represented by a color of a waveform on a purple side (Low) as it weakens. On a left side of FIG. 17(B), holding fingers are shown in correspondence with each row in the matrix M1, the first row in the matrix M1 represents the index finger, the second row in the same represents the middle finger, the third row in the same represents the ring finger, and the left side (the first column side) of the matrix M1 represents a fingertip direction of each finger. Referring to FIG. 17(B) in correspondence with a manner of holding shown in the photograph of FIG. 17(A), since the index finger lightly holds the first row in the matrix M1, the magnitude of the contact pressure p acting on the container is approximately medium, and the squares corresponding to the sensor units U11, U12 and U13 are shown in the blue color. Since the middle finger does not hold the matrix M1, the contact pressure p acting on the container becomes 0, and the squares corresponding to the sensor units U21, U22, and U23 are shown in the purple color. On the other hand, since the ring finger strongly holds the third row in the matrix M1, the contact pressure p acting on the container becomes large, and the squares corresponding to the sensor units U31, U32, and U33 are shown in a bright blue color or red color.

In FIG. 17(B), a direction and magnitude of the shear stress τ acting on the container are represented in the form of a vector using a direction and a length of a line extending from the center of each square toward the outside. As shown in FIG. 17(B), the shear stress in which the shear stresses τx and τy acting on each sensor unit Uij are unified is represented as τij. For example, since a line corresponding to a shear stress τ11 caused due to a finger tip of the index finger is shown long from the center of the square toward the outside in an upper right direction of 45 degrees, it can be understood that it is a rather strong shear stress acting in the upper right direction of 45 degrees. Since the middle finger does not hold the matrix M1, a shear stress τ2j (j=1 to 3) acting on the container becomes 0, and a line is not shown from each square corresponding to the sensor unit U21, U22, or U23 toward the outside. Since a line corresponding to a shear stress τ32 caused by a middle part of the ring finger is shown fairly long from the center of the square toward the outside in the upper right direction of 45 degrees, it can be understood that it is a fairly strong shear stress acting in the upper right direction of 45 degrees. Although a description on any other shear stress τij will be omitted, application of the upward shear stress to the container at the time of holding the container is shown in a very comprehensible manner. Thus, it can be understood that each distribution of the contact pressure p and the shear stress τij is excellently measured without interference of each column.

Figure 18:
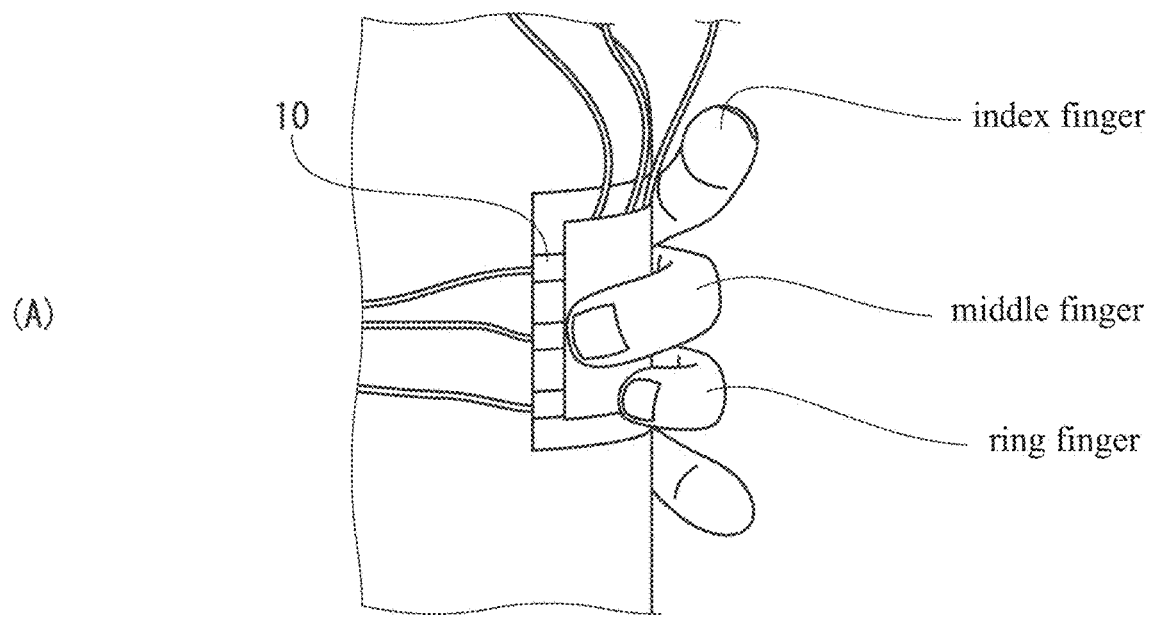
FIG. 18 show another example of a distribution of the contact pressure p and the shear stress τ (τx+τy) when the distribution measuring sensor 10 is bonded to the cylindrical container (a bottle or the like) and lifted up with human fingers, which is a result of Experiment 3.
Figure 18:
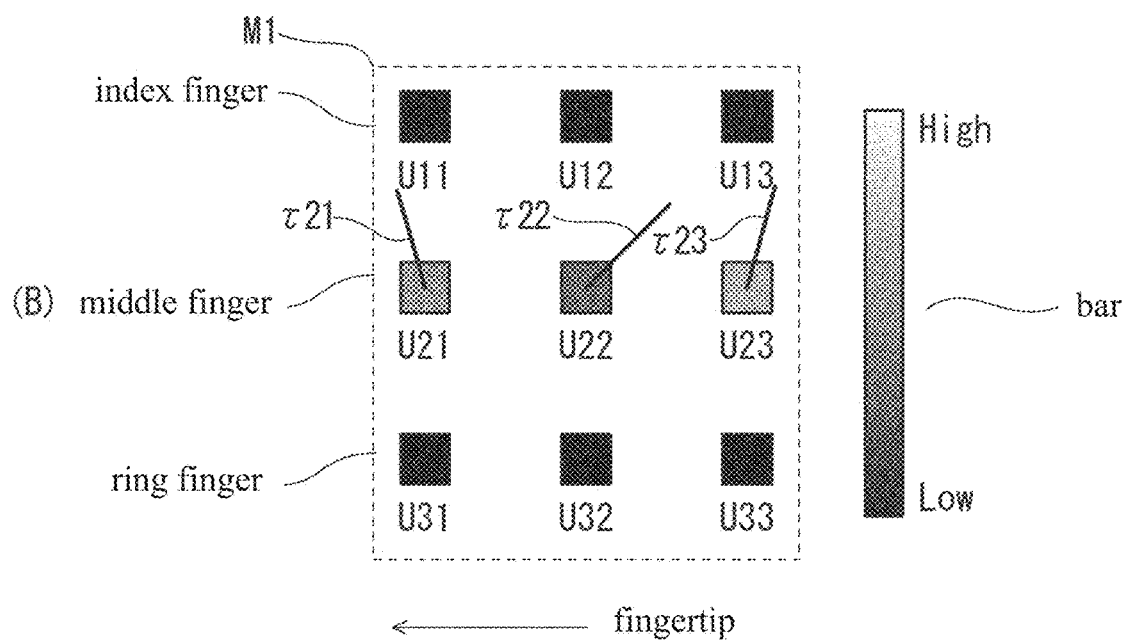

FIG. 18 show another example of a distribution of the contact pressure p and the shear stress τ](τx+τy) when the distribution measuring sensor 10 is bonded to the cylindrical container (a bottle or the like) and lifted up with human fingers, which is a result of Experiment 3. FIG. 18 show the example in which a manner of holding the container shown in FIG. 17 is changed, FIGS. 18(A) and (B) correspond to FIGS. 17(A) and (B), and elements with the same reference signs and names as those in FIGS. 17(A) and (B) have the same meanings, thereby omitting a description thereof. As shown in FIG. 18(A), the distribution measuring sensor 10 is held with the middle finger alone (the second row in the matrix M1), and the index finger and the ring finger are taken off (the first row and the third row in the matrix M1 are not touched).

Referring to FIG. 18(B) in correspondence with a manner of holding shown in the photograph of FIG. 18(A), since the index finger and the ring finger are not holding the matrix the contract pressure p acting on the container becomes 0, and squares corresponding to the sensor units U11 to U13 and U31 to U33 are shown in the purple color. Since the middle finger strongly holds the second row in the matrix M1, the contact pressure p acting on the container increases, and squares corresponding to the sensor units U21 to U23 are shown in the bright blue color or red color.

As shown in FIG. 18(B), since the index finger and the ring finger are not holding the matrix M1, the shear stresses τ1j and τ3j (j=1 to 3) acting on the container become 0, and lines are not displayed from squares corresponding to the sensor units U11 to U13 and U31 to U33 to the outside. On the other hand, since the middle finger is holding the matrix M1, lines are displayed from respective centers of squares corresponding to the respective sensor units U21 to U23 to the outside. In FIG. 18(B), like FIG. 17(B), application of the upward shear stress to the container at the time of holding the container is shown in a very comprehensible manner bike the example in FIG. 17(B), it can be understood that each distribution of the contact pressure p and the shear stress τij is excellently measured without an interference of each column. Thus, it can be understood that the shear stress τ acts on each contacting part alone when the manner of holding is changed. Therefore, it has been demonstrated that the sensor unit Uij can independently measure the shear stress τ.

As described above, the predetermined display format in the display unit 55 is a format in which indication of (e.g., a square) of each sensor unit Uij is arranged in correspondence with the matrix M1, magnitude of the contact pressure p is shown by using each predetermined color (e.g., High to Low are indicated by using colors of a waveform on the red side to a waveform on the purple side) in accordance with each sensor unit Uij, and the shear stress τij which is a combination of the x axis shear stress τx and the y axis shear stress τy is indicated by using a vector.

Thus, according to Embodiment 1 of the present invention, the distribution measuring sensor 10 has the configuration in which the sensor unit Uij which measures a shear stress in each axis (x axis or y axis) direction of a plane and a contact pressure in an axis (z axis) direction perpendicular to the plane is arranged at each element of the matrix M. The sensor unit Uij is constituted of the upper electrode UijH and the lower electrode UijL arranged below the upper electrode UijH through the pressure sensitive material 20 and the like. Each sensor unit Uij (i=1 to m) in the x axis direction arranged in the same column j of the matrix M has each upper electrode UijH (i=1 to in) connected in the column j direction (the x axis direction) in common through the connecting line Cj. Each sensor unit Uij (j=1 to n) in the y axis direction arranged in the same row i of the matrix M has each lower electrode UijL (j=1 to) connected in the row i direction (the y axis direction) in common through the connecting line Ri. Each sensor unit Uij (i=1 to m, j=1 to n. The same suffixes will be adopted hereafter) includes the x axis shear stress measuring unit which measures the shear stress in the x axis direction acting between the upper electrode UijH and the lower electrode UijL, the y axis shear stress measuring unit which measures the shear stress in the y axis direction acting between the upper electrode UijH and the lower electrode UijL, and the contact pressure measuring unit which measures the contact pressure acting in the z axis direction of the upper electrode UijH in a region where the upper electrode UijH (and the lower electrode UijL overlap in the up-and-down direction (the z axis direction). The upper electrode UijH is used for the measurement of the shear stresses τx and τy and the measurement of the contract pressure p in common.

When the shear stress τx acts in the x axis direction to the x axis shear stress measuring unit Uijτx, a shear deformation in the x axis direction occurs in the pressure sensitive material 20x part. Consequently, in the pressure sensitive material 20x part, a distance between the upper electrode UijH and the lower electrode UijLx in a thickness direction becomes rτ which is higher than the original distance r, and hence an electrical resistance in the x axis shear stress measuring unit Uijτx increases. Thus, the shear stress measuring unit Uijτx can measure the shear stress τx in the x axis direction. This is also true in case of the y axis shear stress measuring unit Uijτy. When the contact pressure p acts in the z axis direction to the contact pressure measuring unit Uijp, a deformation in the z axis direction occurs in the pressure sensitive material 20p part. Consequently, in the pressure sensitive material 20p part, a distance between the upper electrode UijH and the lower electrode UijLp in the thickness direction decreases to rp which is smaller than the original distance r, and hence an electrical resistance in the contact pressure measuring unit Uijp is reduced. Thus, the contact pressure Uijp can measure the contact pressure p in the z axis direction. When the shear stress τx in the x axis direction and the shear stress τy in the y axis direction act on the contact pressure measuring unit Uijp, a mutual positional displacement occurs in the x and y axis directions but a deformation in the z axis direction is not produced in the overlapping region in the contact pressure measuring unit Uijp. That is, an electrical resistance value in the z axis direction between the upper electrode UijH and the lower electrode UijLp in the contact pressure measuring unit Uijp does not vary. Therefore, the contact pressure measuring unit Uijp can detect the contact pressure p in the z axis direction alone without being interfered with the shear stress τx in the x axis direction and the shear stress τy in the v axis direction. Thus, the simultaneous measurement of the contact pressure p and the x axis shear stress τx or the y axis shear stress τy is enabled.

The configuration of the distribution measuring sensor system 40 using the distribution measuring sensor 10 according to the present invention can be summarized as follows. The relay unit 41 is configured in such a manner that each connecting line (column line) Cj through which each upper electrode UijH of each sensor unit Uij (i=1 to 4) arranged in the same column j (j=1 to 4) in the matrix M is connected in the column j direction in common can be selected on the basis of the input selection signal SEL. The operation amplifier unit 42 is constituted of each row operation amplifier 42-Ri (i=1 to 4) whose input side is connected to each connecting line (row line) Ri (Rip to the lower electrode UijLp, Rix to the lower electrode UijLx, or Riy to the lower electrode UijLy.) through which the lower electrode UijLp of the contact pressure measuring unit Uijp, the lower electrode UijLx of the x axis shear stress measuring unit Uijτx, and the lower electrode UijLy of the y axis shear stress measuring unit Uijτy of each sensor unit Uij (j=1 to 4) arranged in the same row i (i=1 to 4) in the matrix M are connected in the row i direction respectively in common. The A/D converter 43 has the input side connected to each row operation amplifier unit 42-Ri constituting the operation amplifier unit 42 through each switch 43 SW-Ri (i=1 to 4) of the switch unit 43SW. The computer PC 44 is connected to the output side of the A/D converter 43 and the input side of the relay unit 41.

The operations of the distribution measuring sensor system 40 according to the present invention can be summarized as follows. First, the selection signal SEL to select the connecting line Cj (the column j) is output from the computer PC44 to the relay unit 41, and the connecting line Cj is selected by the relay unit 41 on the basis of the selection signal SEL. The power supply voltage E supplied to the relay unit 41 is applied to each upper electrode UijH of each sensor unit Uij (i=1 to 4) connected to the selected connecting line Cj. A voltage corresponding to a change in electrical resistance based on each of the contact pressure p, the x axis shear stress τx, and the shear stress τy acting on the contact pressure measuring unit Uijp, the x axis shear stress measuring unit Uijτx, and the y axis shear stress measuring unit Uijτy of each sensor unit Uij connected to the selected connecting line Cj is output to each connecting line Rip, Rix, or Riy from each lower electrode UijLp, UijLx, or UijLy of each of the contact pressure measuring unit Uijp, the x axis shear stress measuring unit Uijτx, and the y axis shear stress measuring unit Uijτy. Each output voltage from each row operation amplifier 42-Ri of the operation amplifier unit 42 connected to each connecting line Ri (Rip, Rix, Riy) is output to the A/D converter 43 through each switch 43SW-Ri of the switch unit 43SW. When the output from the A/D converter 43 is output to the computer PC44, the computer PC44 sequentially repeats processing a voltage based on the contact pressure p and the x axis shear stress τx or the y axis shear stress τy from each sensor unit Uij (i=1 to 4) corresponding to one column j selected by the selection signal SEL (later-described conversion processing from a voltage to each pressure and display processing of each pressure) and outputting a selection signal to select a subsequent connecting line Cj+1 (relay control).

The predetermined measurement principle (1) between the contact pressure p acting on the sensor unit Uij in the conversion unit 54 and each output voltage Vip from each operation amplifier OPip connected to the lower electrode UijLp is the measurement principle that, when a relationship between the contact pressure p and the left-hand side (Vp/E) of Expression 5 corresponding thereto is obtained by an experiment in advance, the contact pressure p can be then obtained (converted) from the relationship by measuring the output voltage Vp. That is, measuring the output voltage Vp enables detecting the contact pressure p in the z axis direction alone without being interfered with the shear stress τx in the x axis direction or the shear stress τy in the v axis direction. The predetermined measurement principle (2) between the x axis shear stress τx or the y axis shear stress τy acting on the sensor unit Uij in the conversion unit 54 and each output voltage Viτx or Viτy from each operation amplifier OPix or OPiy connected to each lower electrode UijLx or UijLy is the measurement principle that, when a relationship between the shear stress τ (τx, τy) and the left-hand side $\{(1/V\tau)-(1/Vp)\}\times E$ of Expression 6 corresponding thereto is obtained by an experiment in advance, the shear stress τ can be then obtained (converted) from the relationship by measuring the output voltage Vτ and Vp. It is possible to discriminate an acting direction of the shear stress τ on the basis of the measured shear stresses τx and τy. As described above, according to the distribution measuring sensor system 40 of the present invention, the contact pressure p and the x axis shear stress τx or the y axis shear stress τy on the sensor unit Uij can be simultaneously measured.

The predetermined display format in the display unit 55 is the format in which indication (e.g., a square) of each sensor unit Uij is arranged in correspondence with the matrix Mi, magnitude of the contact pressure p is indicated by using each predetermined color (e.g., High to Low are indicated by colors having a waveform on the red side to a waveform on the purple side) in accordance with each sensor unit Uij, and the shear stress τij which is a combination of the x axis shear stress τx and the y axis shear stress τy is indicated by a vector.

As described above, the distribution measuring sensor 10 according to the present invention has enabled arranging many measurement points at intersection points (elements of the matrix M) of the upper and lower electrodes by coupling many sensor units Uij (the measurement points) through the connecting lines Ci and Ri. With this matrix-shaped configuration, information of the contact pressure and the shear stress is not obtained by scanning the measurement points one by one, but each row i (i=1 to m) is selected by sequentially selecting each switch S43SW-Ri as described above in a state where one column j in the matrix M is selected, thereby acquiring information of each sensor unit Uij (an intersection point). Moreover, it is possible to carry out matrix-type scanning to obtain the information of each sensor unit Uij by selecting a subsequent column j+1 with the use of the repetition unit 56 like the column j. Consequently, according to the distribution measuring sensor system 40 of the present invention, it is possible to provide the distribution measuring sensor system with a high resolution and the like which have characteristics of the thin flexible distribution measuring sensor 10 applicable to the measurement of the contact pressure p and the shear stress τ acting on an interface between a living body (fingers) and an object (a container), can greatly reduce a wiring region even if many sensor units Uij are integrated to grasp a distribution of a tactile sense, simplify the design, suppress an increase in manufacturing costs, and are applicable to the interface between the living body and the object.

Embodiment 2

Figure 19:
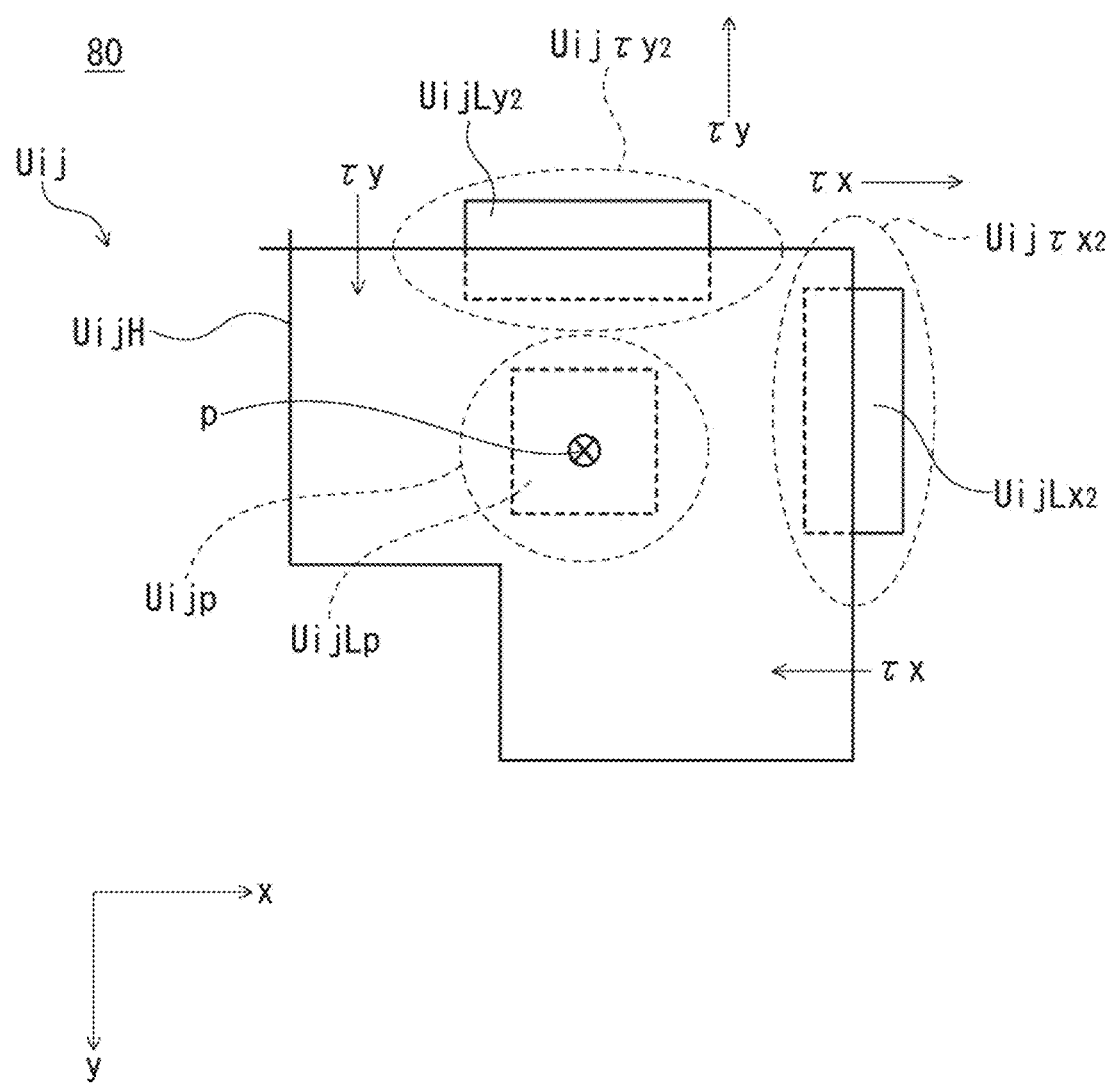
FIG. 19 shows another shape example of the sensor unit Uij in a plan view.

FIG. 19 shows another shape example of the sensor unit Uij in a plan view. In FIG. 19, parts with the same reference signs as those in FIG. 5 denote the same elements, and hence a description thereof will be omitted. In FIG. 5, the lower right side portion of the upper electrode UijH was taken as the x axis parallel portion of the upper electrode UijH, and the upper left side portion of the upper electrode UijH was taken as the y axis parallel portion of the same. Likewise, the upper side portion of the upper electrode UijH can be taken as the other x axis parallel portion of the upper electrode UijH and the right side portion of the upper electrode UijH can be taken as the other y axis parallel portion of the same. A point that a sensor unit Uij in FIG. 19 is different from the sensor unit Uij in FIG. 5 lies in that the x axis shear stress measuring unit Uijτx in FIG. 5 is set to the other y axis parallel portion as an x axis shear stress measuring unit Uijτx2, and the y axis shear stress measuring unit Uijτy in FIG. 5 is set to the other x axis parallel portion as a y axis shear stress measuring unit Uijτy2. As shown in FIG. 19, a lower electrode UijLx2 was designed in such a manner that an area (which is preferable a half area) of a part of the lower electrode UijLx2 overlaps an area of a part of an upper electrode UijH vertically (in a z axis direction) in the other y axis parallel portion of the upper electrode UijH. A lower electrode UijLy2 was designed in such a manner that an area (which is preferably a half area) of a part of the lower electrode UijLy overlaps an area of a part of the upper electrode UijH vertically (in the z axis direction) in the other x axis parallel portion of the upper electrode A measuring method when a shear stress τx in an x axis direction acts on the x axis shear stress measuring unit Uijτx2 and a measuring method when a shear stress τx in a y axis direction acts on the y axis shear stress measuring unit Uijτy2 are the same as those of the sensor unit Uij in FIG. 5, and hence a description thereof will be omitted. A setting of a contact pressure measuring unit Uijp is the same as that of the sensor unit Uij in FIG. 5, and hence a description thereof will be omitted.

Thus, according to Embodiment 2 of the present invention, as another shape of the sensor unit Uij of Embodiment 1, the x axis shear stress measuring unit Uijτx2 can be set to the other y axis parallel portion, and the y axis shear stress measuring unit Uijτy2 can be set to the other x axis parallel portion. In this setting, like Embodiment 1, the x axis shear stress measuring unit Uijτx2 can detect the shear stress τx in the x axis direction alone without being interfered with the shear stress τy in the y axis direction, and the y axis shear stress measuring unit Uijτy2 can detect the shear stress τy in they axis direction alone without being interfered with the shear stress τx in the x axis direction. Consequently, on the basis of the measured shear stresses τx and τy, an acting direction of the shear stress τ (=τx+τy) can be discriminated. The contact pressure measuring unit Uijp can detect the contact pressure p in the z axis direction alone without being interfered with the shear stress τx in the x axis direction and the shear stress τy in the y axis direction. Thus, in the sensor unit Uij according to Embodiment 2, the contact pressure p and the x axis shear stress τx or the y axis shear stress τy can be likewise simultaneously measured.

Embodiment 3

Figure 20:
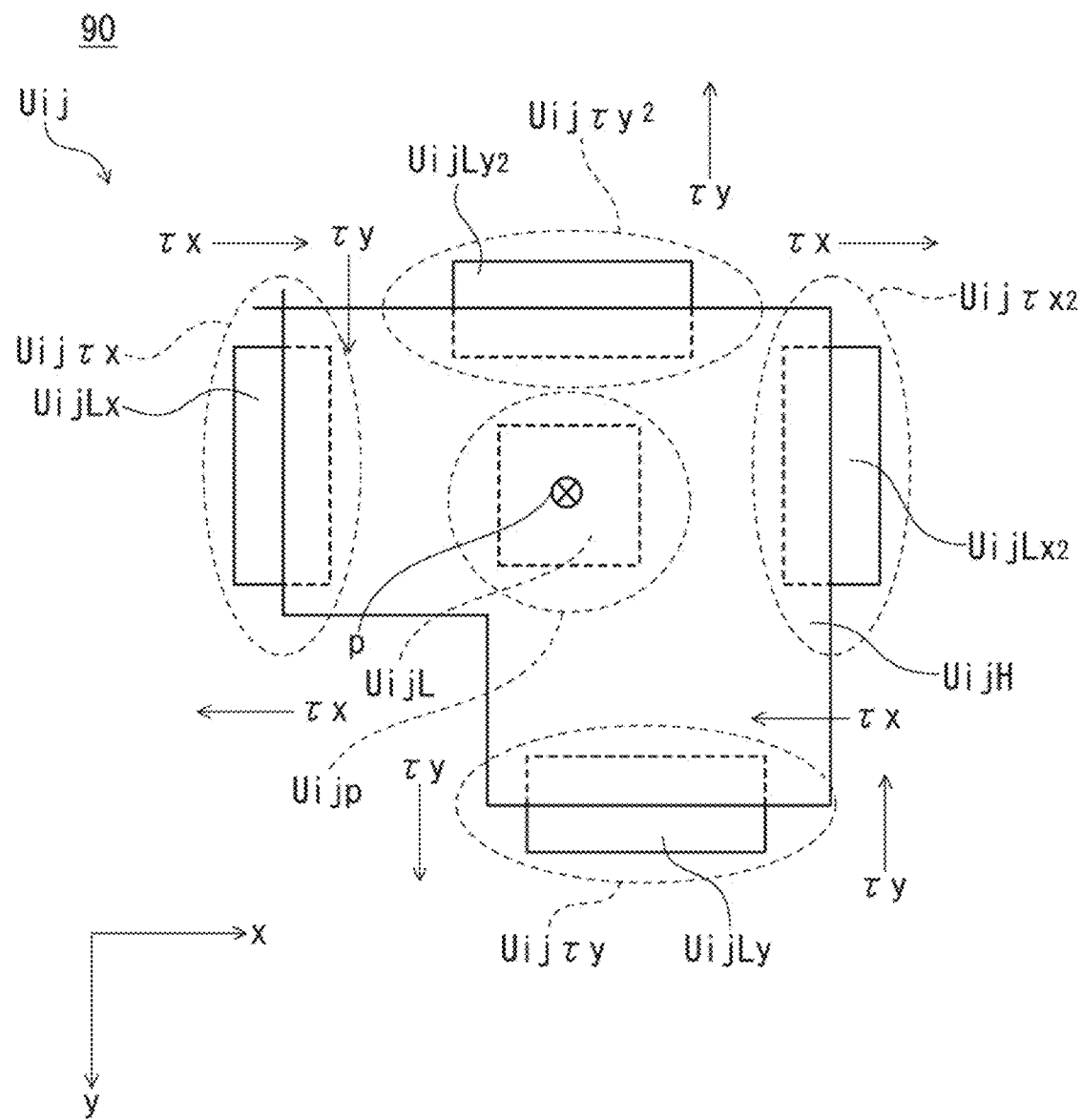
FIG. 20 shows another shape example of the sensor unit Uij in a plan view.

FIG. 20 shows another shape example of the sensor unit Uij in a plan view. In FIG. 20, parts with the same reference signs as those in FIG. 5 and FIG. 9 denote the same elements, and hence a description thereof will be omitted. A sensor unit Uij shown in FIG. 20 is designed by combining the sensor unit Uij in FIG. 5 with the sensor unit Uij in FIG. 19. As shown in FIG. 20, a shear stress τx in the x axis direction is measured by an x axis shear stress measuring unit Uijτx and an x axis shear stress measuring unit Uijτx2, and a shear stress τy in the y axis direction is measured by a y axis shear stress measuring unit Uijτy and a y axis shear stress measuring unit Uijτy2. A measuring method in each measuring unit is the same as those in Embodiments 1 and 2, and hence a description thereof will be omitted. As the shear stress τx in the x axis direction, an average of two, i.e., the shear stress measured by the x axis shear stress measuring unit Uijτx and the shear stress measured by Uijτx2 can be taken. Alternatively, it may be acquired by appropriately multiplying a weight to two measurement values. The same applies to the shear stress τy in the y axis direction. A setting of a contact pressure measuring unit Uijp is the same as that of the sensor unit Uij in FIG. 5, and hence a description thereof will be omitted.

Thus, according to Embodiment 3 of the present invention, the shape of the sensor unit Uij of Embodiment 1 can be combined with another shape of the sensor unit Uij of Embodiment 2. That is, the number of the x axis shear stress measuring unit Uijτx and the like and the y axis shear stress measuring unit Uijτy and the like can be increased. In the shape of Embodiment 3, like Embodiments 1 and 2, the shear stress measuring units Uijτx and Uijτx2 can detect the shear stress τx in the x axis direction alone without being interfered with the shear stress τy in the y axis direction, and the shear stress measuring units Uijτy and Uijτy2 can detect the shear stress τy in the y axis direction alone without being interfered with the shear stress τx in the x axis direction. Consequently, on the basis of an average or the like of the two measured shear stresses τx and an average or the like of the two shear stresses τy, an acting direction of the combined shear stress τ can be discriminated. The contact pressure measuring unit Uijp can detect a contact pressure p in the z axis direction alone without being interfered with the shear stress τx in the x axis direction and the shear stress τy in the y axis direction. Thus, in the sensor unit Uij of Embodiment 2, the contact pressure p and the x axis shear stress τx or the y axis shear stress τy can be likewise simultaneously measured.

The number of the x axis shear stress measuring unit Uijτx and the like or the number of they axis shear stress measuring unit Uijτy and the like is not restricted to two, and an arbitrary number of respective units may be provided in accordance with a target to be measured. A shape of an upper electrode UijH is not restricted to the shape lacking the lower left corner as described above. A shape of the entire upper electrode UijH may be an arbitrary shape such as a triangle or a circle as long as an x axis parallel portion and a y axis parallel portion are provided to parts of the shape of the upper electrode UijH in advance and the y axis shear stress measuring unit Uijτy and the x axis shear stress measuring unit Uijτy are set to such parts.

Embodiment 4

Figure 21:
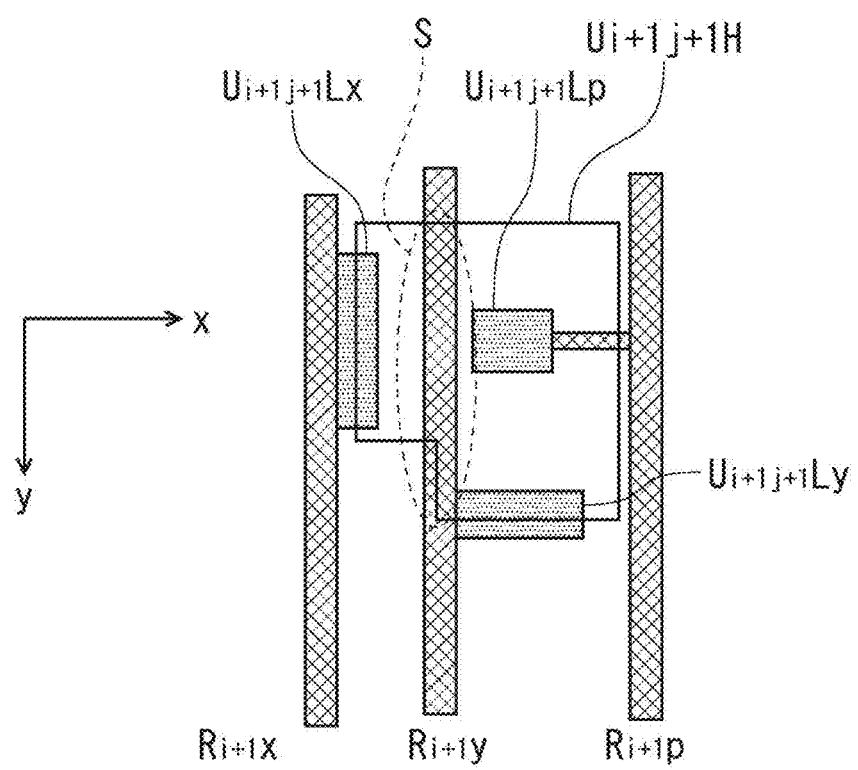
FIG. 21 illustrates various influences of an area where a connecting line Ri+1y and an upper electrode Ui+1j+1H vertically overlap in each of the foregoing embodiments.

FIG. 21 illustrates various influences of an area where a connecting line Ri+1y and an upper electrode Ui+1j+1H vertically overlap in each of the foregoing embodiments. FIG. 21 is a view of a part taken out from FIG. 7(B), and parts with the same reference numerals as those in FIG. 7 denote the same elements, thereby omitting a description thereof. As shown in FIG. 21, a possibility that an area S where a connecting line Ri+1y (a lead line Ri+1y) through which a lower electrode Ui+1j+1Ly of a y axis shear stress measuring unit Ui+1j+1τy is connected in a row i+1 direction and the upper electrode Ui+1j+1H vertically overlap influences a change in area of a region where the upper electrode Ui+1j+1H and a part of a lower electrode Ui+1j+1Lx and a part of the lower electrode Ui+1j+1Ly overlap (which is therefore a change in distance in a thickness direction and a change in electrical resistance) when shear stresses τx and τy act can be considered. This influence barely matters when a line width of the connecting line Ri+1y is sufficiently small. However, to prevent the influence, an insulating layer is applied to the connecting line Ri+1y in the overlapping area S part as required. That is, the area S part adopts the structure in which the connecting line Ri+1y, the insulating layer, a pressure sensitive material 20y, and the upper electrode Ui+1j+1H are provided in the z axis direction.

Embodiment 5

Figure 22:
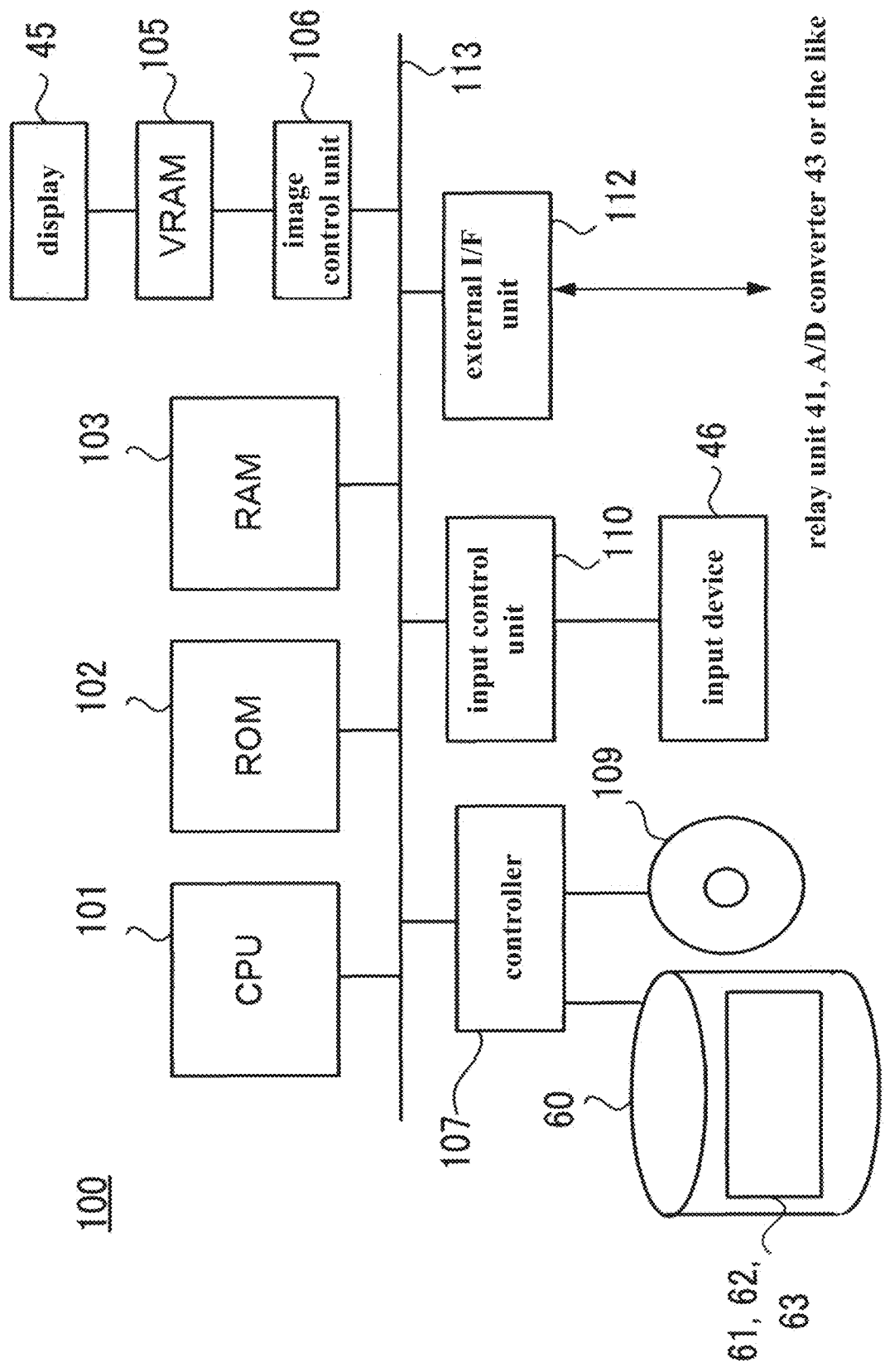
FIG. 22 is a block diagram showing an internal circuit 100 of a computer PC44 which executes the distribution measuring program according to the present invention.

FIG. 22 is a block diagram showing an internal circuit 100 of a computer PC44 which executes the distribution measuring program according to the present invention. As shown in FIG. 22, a CPU 101, a ROM 102, a RAM 103, an image control unit 106, a controller 107, an input control unit 109, and an external I/F unit 112 are connected to a bus 113. In FIG. 22, the above-described distribution measuring program according to the present invention is recorded in the ROM 102, a recording region 60 of a disk and the like, or a recording medium (including a detachable recording medium) such as a DVD or a CD-ROM 109 and the like. The contact pressure recording area 61, the x axis shear stress recording area 62, the y axis shear stress recording area 63, and the like can be recorded in the disk 60. The distribution measuring program is loaded to the RAM 103 from the ROM 102 through the bus 113 or from the disk 60 or the recording medium, the DVD or the CD-ROM 109 and the like through the controller 107 and the bus 113. The image control unit 106 transmits image data of various images (FIG. 17(B), FIG. 18(B)) and the like displayed in a display 45 to a VRAM 105. The display 45 displays the data and the like transmitted from the VRAM 105. The VRAM 105 is an image memory having a capacity corresponding to a data capacity for one screen of the display 45. An input device 46 is an input device such as a mouse or a keyboard or the like to perform, e.g., input to the computer PC44, and the input control unit 110 is connected to the input device 46 to perform, e.g., input control. The external unit 112 has an interface function at the time of connecting with the outside (a relay unit 41, an A/D converter 43, or the like) of the computer PC44 (the CPU 101).

As described above, when the computer PC44 (the CPU 101) executes the distribution measuring program of the present invention, the object of the present invention can be achieved. The distribution measuring program can be supplied to the computer PC44 (the CPU 101) in the form of a recording medium, e.g., the DVD or the CD-ROM 109, and the recording medium, e.g., the DVD or the CD-ROM 109 having the distribution measuring program recorded therein likewise constitutes the present invention. As the recording medium having the distribution measuring program recorded therein, it is possible to use, e.g., a memory card, a memory stick, or an optical disk or the like besides the above-described recording medium.

Embodiment 6

Figure 3:
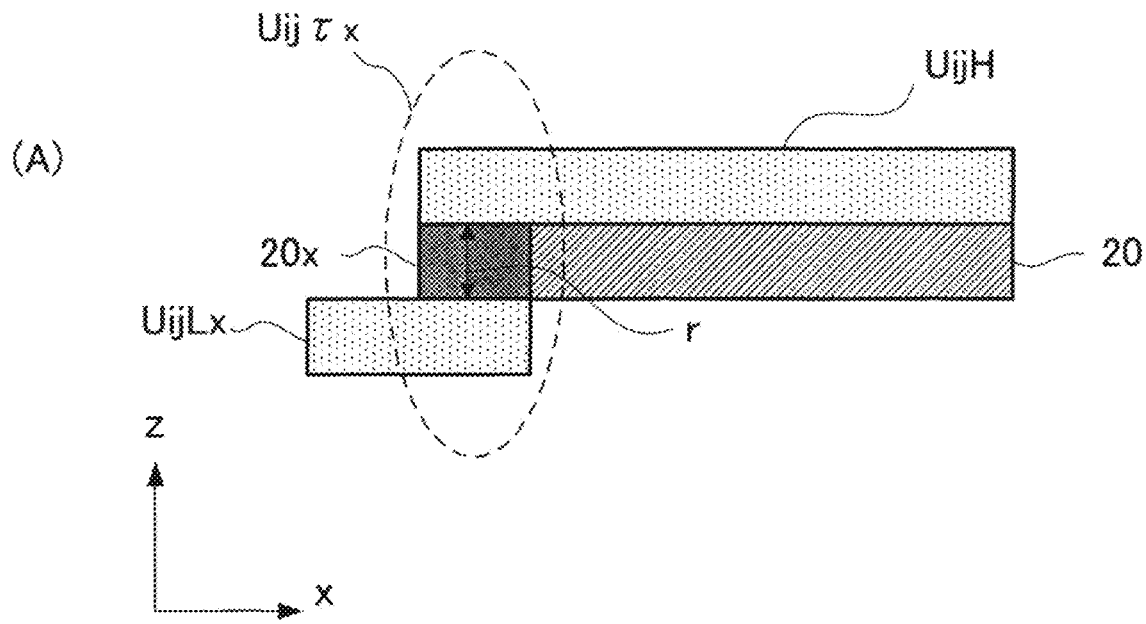
FIGS. 3(A) and (B) are vertical cross-sectional views of the vicinity of the x axis shear stress measuring unit UijτX of the sensor unit Uij shown in FIG. 2.
Figure 3:
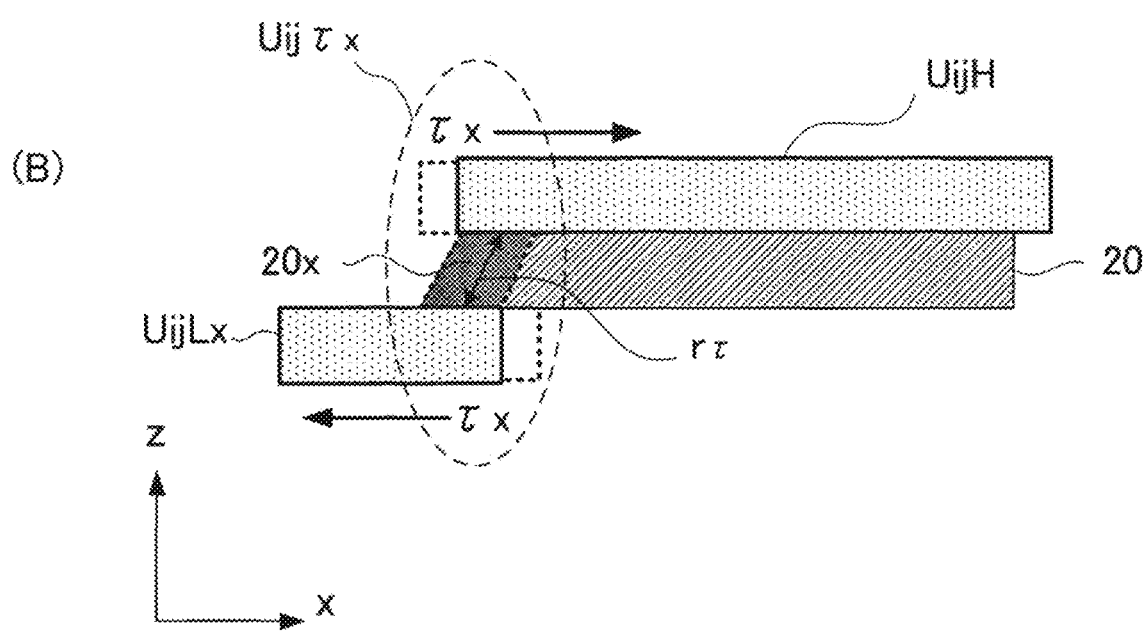
Figure 23:
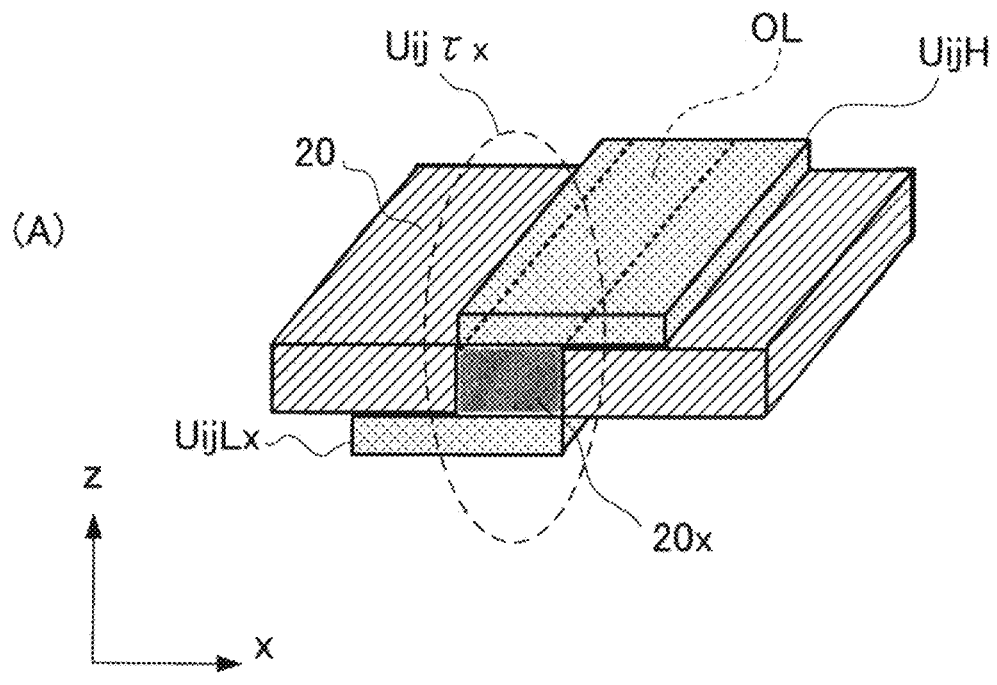
FIGS. 23(A) and (B) are vertical cross-sectional views of the vicinity of an x axis shear stress measuring unit Uijτx of a sensor unit Uij which is substantially the same as that in FIGS. 3(A) and (B).
Figure 23:
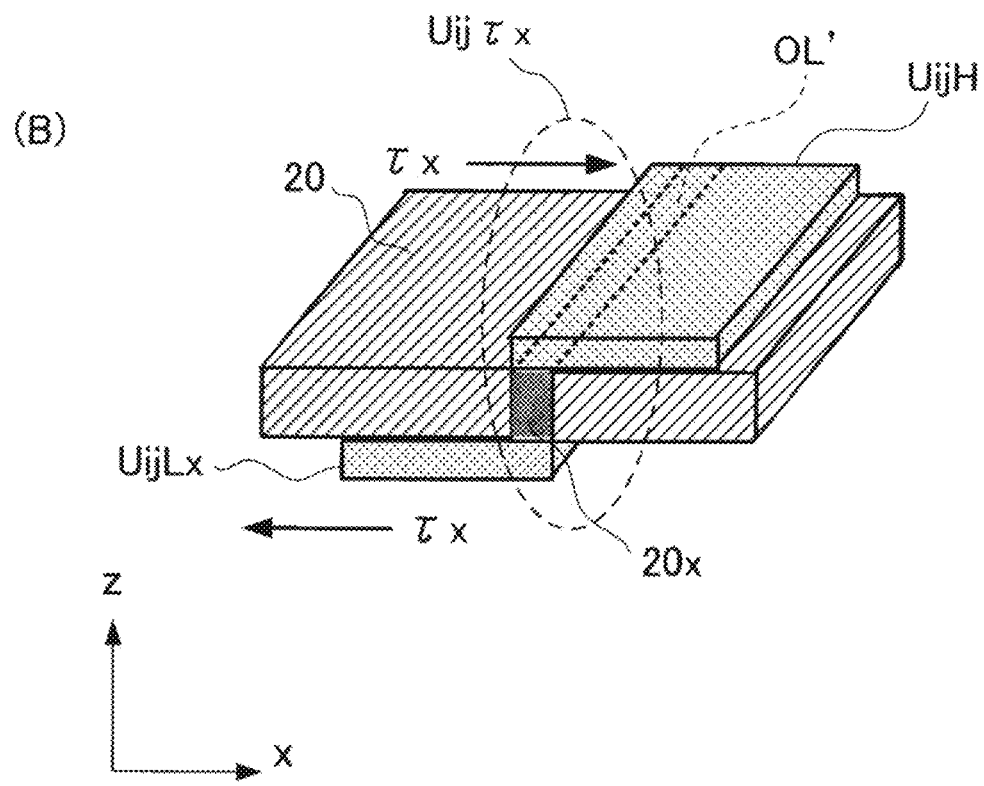

FIGS. 23(A) and (B) are vertical cross-sectional views of the vicinity of an x axis shear stress measuring unit Uijτx of a sensor unit Uij which is substantially the same as that in FIGS. 3(A) and (B), and parts with the same reference signs as those in FIGS. 3(A) and (B) denote the same elements, thereby omitting a description thereof. As shown in FIG. 23(A), an area (an area of the above-described overlapping region) w e a pressure sensitive material 20x of the x axis shear stress measuring unit Uijτx overlaps an upper electrode UijH side is OL. Although an area where the pressure sensitive material 20x overlaps a lower electrode UijLx side is not shown, it is likewise OL. Here, when a shear stress τx acts on the x axis shear stress measuring unit Uijτx in positive and negative directions of an x axis, the upper electrode UijH side shifts in the positive direction of the x axis and the lower electrode UijLx side shifts in the negative direction of the x axis as shown in FIG. 23(B). Up to this point, this embodiment is the same as Embodiment 1 (see FIG. 3), but the area of the overlapping area decreases from OL to OL' as a result of shifts of both the electrodes (a change in positional relationship) in this embodiment 6, and hence an electrical resistance value in the x axis shear stress measuring unit Uijτx increases. That is, when the shear stress τx in the positive and negative directions of the x axis acts, the shear stress measuring unit Uijτx can measure the shear stress τx in the x axis direction on the basis of a change (an increase) in electrical resistance value due to a decrease in area of the overlapping region (from OL to OL').

In Embodiment 1 described above, when the shear stress τx in the positive and negative directions of the x axis acts on the shear stress measuring unit Uijτx, the upper electrode UijH side shifts in the positive direction of the x axis and the lower electrode UijLx side shift in the negative direction of the x axis as shown in FIG. 3(B). As a result of the shifts of both the electrodes change in positional relationship), on the basis of a shear deformation of the pressure sensitive material 20 in the x axis direction in the overlapping region, i.e., a change in distance between the upper electrode UijH and the lower electrode UijLx in the thickness direction (an increase from r to rτ), the shear stress τx in the x axis direction can be measured. In this Embodiment 6, as a result of the shifts of both the electrodes (the change in positional relationship), even if a shear deformation of the pressure sensitive material 20x in the x axis direction in the overlapping region is not produced, the shear stress measuring unit Uijτx can measure the shear stress τx in the x axis direction on the basis of a change in electrical resistance value due to a change in area of the pressure sensitive material 20x in the x axis direction (a decrease from OL to OL') in the overlapping region. To sum up, the x axis shear stress measuring unit Uijτx can measure the shear stress τx in the x axis direction on the basis of a change in electrical resistance value of the pressure sensitive material 20x in the overlapping region when the shear stress in the x axis direction acts.

The same applies to the case where the shear stress τy acts in the y axis direction on the y axis spar stress measuring unit Uijτy, the x axis in FIGS. 23(A) and (B) can be replaced with the y axis, and the reference sign x can be replaced with y. That is, when the shear stress τy acts in the positive and negative directions of the y axis on the y axis shear stress measuring unit Uijτy, the upper electrode side shifts in the positive direction of the y axis, and the lower electrode UijLy side shifts in the negative direction of the y axis. Up to this point, this embodiment is the same as Embodiment 1 (see FIG. 3), but the area of the overlapping area (not shown as to the y axis shear stress measuring unit Uijτy) decreases from OL to OL' as a result of shifts of both the electrodes (a change in positional relationship) in this Embodiment 6, and hence an electrical resistance value in the y axis shear stress measuring unit Uijτy increases. That is, when the shear stress τy in the positive and negative directions of the y axis acts, the shear stress measuring unit Uijτy can measure the shear stress τy in the y axis direction on the basis of a change (an increase) electrical resistance value due to a decrease in area of the overlapping region (from OL to OL'). In this Embodiment 6, as a result of the shifts of both the electrodes (the change in positional relationship), even if a shear deformation of the pressure sensitive material 20y in the y axis direction in the overlapping region is not produced, the shear stress measuring unit Uijτy can measure the shear stress τy in the y axis direction on the basis of a change in electrical resistance value due to a change in area of the pressure sensitive material 20y (not shown) in the y axis direction (a decrease from OL to OL') in the overlapping region. To sum up, they axis shear stress measuring unit Uijτy can measure the shear stress τy in the y axis direction on the basis of a change in electrical resistance value of the pressure sensitive material 20y in the overlapping region when the shear stress in the y axis direction acts.

INDUSTRIAL APPLICABILITY

As a utilization example of the present invention, application to measurement of a contact pressure and a shear stress acting on an interface between a living body and an object, especially measurement of a distribution of a tactile sense to enable high spatial resolution is possible.

EXPLANATIONS OF LETTERS OR NUMERALS 10 a distribution measuring sensor, 20,20x,20p pressure sensitive materials, 40 a distribution measuring sensor system, 41 a relay unit, 42 an operation amplifier unit, 42-R1, 42-R2, 42R3, 42-R4, 42-Ri a row operation amplifier unit, 43SW a switch unit, 43SW-R1, 43SW-R2, 43SW-R3, 43SW-R4, 43SW-Rip,43SW-Rix, 43SW-Riy a switch, an A/D converter, 44 a computer 45 a display, 46 an input device, 50F a block of functions and others, 51 a selection signal control unit, 52 an A/D converter, 53 voltage data recording unit, 54 a conversion unit, 55 a display unit, 56 a repetition unit, 60 a recording region, 61 a contact pressure recording area, 62 an x axis shear stress recording area, 63 a y axis shear stress recording area, 70 a calibration device, 71,72,73 an actuator, 74 an X-Y stage, 76 a compression type load cell, 100 an internal circuit, 101 a CPU, 102 a ROM, 103 a RAM, 105 a VRAM, 106 an image control unit, 107 a controller, 109 a recording medium, 110 an input control unit, 112 an external I/F unit 113 a bus.

The invention claimed is:

1. A distribution measuring sensor having a configuration in which sensor units which measure a shear stress in each axis (an x axis, a y axis) direction of a plane and a contact pressure in an axis (a z axis) direction perpendicular to the plane are arranged in a matrix form,
    wherein said sensor unit comprises:
    an upper electrode which is used for measurement of the shear stress and the contact pressure in common and a lower electrode which is arranged through the upper electrode and a pressure sensitive material and is constituted of electrodes individually used for measurement of the shear stress and that of the contact pressure;
    an x axis shear stress measuring unit which measures the shear stress in the x axis direction acting between said upper electrode and said lower electrode;
    a y axis shear stress measuring unit which measures the shear stress in the y axis direction acting between said upper electrode and said lower electrode; and
    a contact pressure measuring unit which measures the contact pressure acting in the z axis direction of said upper electrode,
    wherein each upper electrode of each sensor unit arranged on the same column of said matrix is connected in the column direction in common, and respective lower electrode sides of said x axis shear stress measuring unit, said y axis shear stress measuring unit, and said contact pressure measuring unit of each sensor unit arranged in the same row of said matrix are connected in the row direction in common.

2. The distribution measuring sensor according to claim 1, wherein each of said x axis shear stress measuring unit and said y axis shear stress measuring unit has a region where a part of said upper electrode and a part of said lower electrode side of each measuring unit overlap vertically (in the z axis direction),
    said x axis shear stress measuring unit measures the shear stress in the x axis direction on the basis of a change in electrical resistance value due to a shear deformation in the x axis direction of the pressure sensitive material in the overlapping region when the shear stress in the x axis direction acts,
    said y axis shear stress measuring unit measures the shear stress in the y axis direction on the basis of a change in electrical resistance value due to a shear deformation in the y axis direction of the pressure sensitive material in said overlapping region when the shear stress in the y axis direction acts, and
    said contact pressure measuring unit has a region where a part of said upper electrode and all of said lower electrode side of sad contact pressure measuring unit overlap vertically (in the z axis direction), and measures the contact pressure in the z axis direction on the basis of a change in electrical resistance value due to a deformation in the z axis direction of the pressure sensitive material in said overlapping region when the contact pressure in the z axis direction acts.

3. The distribution measuring sensor according to claim 2, wherein said upper electrode has a predetermined shape which has an x axis parallel portion having a side parallel to the x axis direction and a y axis parallel portion having a side parallel to the y axis direction,
    the lower electrode side of said x axis shear stress measuring unit has a rectangular shape smaller than said upper electrode, and an area of a part of the rectangular shape overlaps said y axis parallel portion vertically (in the z axis direction), the lower electrode side of said y axis shear stress measuring unit has a rectangular shape smaller than said upper electrode, and an area of a part of the rectangular shape overlaps said x axis parallel portion vertically (in the z axis direction), and the lower electrode side of said contact pressure measuring unit has a predetermined shape smaller than said upper electrode, and an area of the entire predetermined shape overlaps said upper electrode.

4. The distribution measuring sensor according to claim 1, wherein a copper-clad polyimide film is used for said upper electrode and said lower electrode, and a conductive polymer material is used for said pressure sensitive ingredient.

5. The distribution measuring sensor according to claim 1, wherein said plane is an interface between a living body and a solid substance.

6. A distribution measuring sensor system using the distribution measuring sensor according to claim 1, comprising:

a relay unit configured to enable selecting each column line through which each upper electrode of each sensor unit arranged in the same column of said matrix are connected in the column direction in common on the basis of an input selection signal;

an inverting amplifier circuit unit constituted of each inverting amplifier circuit whose input side is connected to each row line through which a lower electrode of a contact pressure measuring unit, a lower electrode of an x axis shear stress measuring unit, and a lower electrode of a y axis shear stress measuring unit of each sensor unit arranged in the same row of the matrix are connected in the row direction in common;

an A/D conversion unit whose input side is connected to each inverting amplifier circuit constituting said inverting amplifier circuit unit; and a computer connected to an output side of said A/D conversion unit and an input side of said relay unit, wherein a selection signal is output from said computer to said relay unit, a column line is selected by said relay unit on the basis of the selection signal, a power supply voltage supplied to said relay unit is applied to each upper electrode of each sensor unit connected to the column line, a voltage based on each of a contact pressure, an x axis shear stress, and a y axis shear stress acting on said contact pressure measuring unit, said x axis shear stress measuring unit, and said y axis shear stress measuring unit of each sensor unit connected the column line is output to each row line from each lower electrode of each of said contact pressure measuring unit, said x axis shear stress measuring unit, and said y axis shear stress measuring unit, an output voltage from each inverting amplifier circuit of said inverting amplifier circuit unit connected to each row line is output to said A/D conversion unit, an output from said A/D conversion unit is output to said computer, and said computer thus repeats processing the voltage based on the contact pressure, the x axis shear stress, and the y axis shear stress from each sensor unit corresponding to one column selected by the selection signal and outputting a selection signal to select a subsequent column line.

7. The distribution measuring sensor system according to claim 6, wherein an input side of said A/D conversion unit is connected to each inverting amplifier circuit constituting said inverting amplifier circuit unit through each switch, and the computer comprises:

selection signal controlling means for outputting a selection signal to select a designated column of said matrix to said relay unit;

A/D conversion unit controlling means for sequentially inputting to said A/D conversion unit an output voltage from each inverting amplifier circuit of said inverting amplifier circuit unit based on a contact pressure, an x axis shear stress, and a y axis shear stress from each sensor unit corresponding to one column in regard to a column selected by the selection signal output from said selection signal controlling means by selecting each switch of said A/D conversion unit;

voltage data recording means for recording voltage data based on the contact pressure, the x axis shear stress, and the y axis shear stress from each sensor unit which have been input to said A/D conversion unit by said A/D conversion unit controlling means and subjected to A/D conversion by said A/D conversion unit in a contact pressure recording region, an x axis shear stress recording region, and a y axis shear stress recording region for each sensor unit;

converting means for converting each voltage data recorded in the contact pressure recording region, the x axis shear stress recording region, and the y axis shear stress recording region for each sensor unit by said voltage data recording means into the contact pressure, the x axis shear stress, and the y axis shear stress acting on each sensor unit on the basis of a relationship according to predetermined measurement principles between the contact pressure, the x axis shear stress, and the y axis shear stress acting on said sensor unit and each output voltage from each inverting amplifier circuit connected to each lower electrode;

displaying means for displaying the contact pressure, the x axis shear stress, and the y axis shear stress acting on each sensor unit which have been converted by said converting means in an output display unit of said computer in a predetermined display format; and repeating means for repeating processing from said selection signal controlling means by designating a subsequent column of the column selected by the selection signal output from said selection signal controlling means.

8. The distribution measuring sensor system according to claim 7, wherein the predetermined measurement principle between the contact pressure acting on said sensor unit and the output voltage from the inverting amplifier circuit connected to the lower electrode in said converting means is a measurement principle that an output voltage ($V_p$) based on the contact pressure is representable by using a resistance variation ($\Delta R_p$) alone based on the contact pressure like the following Expression 1:

[Numerical formula 1]

$$\frac{V_p}{E} = \frac{R}{(R_0 + \Delta R_p)} \quad (1)$$

where the power supply is (E), the output voltage from the inverting amplifier circuit of said inverting amplifier circuit unit based on the contact pressure is ($V_p$), a feedback resistance of the inverting amplifier circuit is (R), a resistance between the upper electrode and the lower electrode at the time of no load of a pressure ($R_0$), and the resistance variation between the upper electrode and the lower electrode at the time of loading of the contact pressure is ($\Delta R_p$).

9. The distribution measuring sensor system according to claim 7, wherein the predetermined measurement principle between the x axis shear stress or the y axis shear stress acting on said sensor unit and each output voltage from each inverting amplifier circuit connected to the lower electrode in said converting means is a measurement principle that an output voltage ($V_p$) based on the contact pressure and an output voltage ($V_\tau$) based on the shear stress are representable by using a resistance variation ($\Delta R_\tau$) alone based on the shear stress like the following Expression 2:

[Numerical formula 2]

$$\left(\frac{1}{V_\tau} - \frac{1}{V_p}\right) \times E = -\frac{\Delta R_\tau}{R} \quad (2)$$

where the output voltage is (E), the output voltage from the inverting amplifier circuit of said inverting amplifier circuit unit based on the contact pressure is ($V_p$), the output voltage from the inverting amplifier circuit of said inverting amplifier circuit unit based on the shear stress is ($V\tau$: a generic term for $V_{\tau x}$ corresponding to the x axis and $V_{\tau y}$ corresponding to the y axis), a feedback resistance of the inverting amplifier circuit is (R), and the resistance variation between the upper electrode and the lower electrode at the time of loading of the shear stress is ($\Delta R_\tau$: a generic term for $\Delta R_{\tau x}$ corresponding to the x axis and $\Delta R_{\tau y}$ corresponding to the y axis).

10. The distribution measuring sensor system according to claim 7, wherein the predetermined display format in said displaying means arranges indications of the sensor units in correspondence with said matrix, shows magnitude of the contact pressure by using each predetermined color in accordance with each sensor unit, and shows shear stress which is a combination of the x axis shear stress and the y axis shear stress by using a vector.

11. A computer-readable non-transitory medium upon which is embodied a sequence of programmed instructions which, when executed by a processor, cause said processor to perform distribution measuring with a distribution measuring sensor system according to claim 6, the distribution measuring sequence of programmed instructions configured to cause said processor to perform:

a selection signal controlling step of outputting a selection signal to select a designated column of said matrix to said relay unit;

an A/D conversion unit controlling step of sequentially inputting to said A/D conversion unit an output voltage from each inverting amplifier circuit of said inverting amplifier circuit unit based on a contact pressure, an x axis shear stress, and a y axis shear stress from each sensor unit corresponding to one column by selecting each switch of said A/D conversion unit with regard to the column selected by the selection signal output at said selection signal controlling step;

a voltage data recording step of recording voltage data based on the contact pressure, the x axis shear stress, and the y axis shear stress from each sensor which have been input to said A/D conversion unit and subjected to A/D conversion by said A/D conversion unit at said A/D conversion unit controlling step in a contact pressure recording region, an x axis shear stress recording region, and a y axis shear stress recording region for each sensor unit;

a converting step of converting each voltage data recorded in the contact pressure recording region, the x axis shear stress recording region, and the y axis shear stress recording region for each sensor unit at said voltage data recording step into the contact pressure, the x axis shear stress, and the y axis shear stress acting on each sensor unit on the basis of a relationship according to predetermined measurement principles between the contact pressure, the x axis shear stress, and the y axis shear stress acting on said sensor unit and each output voltage from each inverting amplifier circuit connected to the each lower electrode;

a displaying step of displaying the contact pressure, the x axis shear stress, and the y axis shear stress acting on each sensor unit which have been converted at said converting step in an output display unit of said computer in a predetermined display format; and a repeating step for repeating processing from said selection signal controlling step by designating a subsequent column of the column selected by the selection signal output at said selection signal controlling step.

* * * * *

UNITED STATES PATENT AND TRADEMARK OFFICE
CERTIFICATE OF CORRECTION

PATENT NO. : 10,859,449 B2
APPLICATION NO. : 16/347130
DATED : December 8, 2020
INVENTOR(S) : Kazuhiko Sasagawa It is certified that error appears in the above-identified patent and that said Letters Patent is hereby corrected as shown below:

In the Specification

Column 11, Line 9-10:
Please change "Uij$\tau$y unit" to -- unit Uij$\tau$y --.

Column 12, Line 29-30:
Please change "side" to -- deformation --.

Column 14, Line 39-40:
Please change "LG3" to -- L3G --.

Column 22, Line 20:
Please change "14" to -- S14 --.

Column 22, Line 23:
Please change "12" to -- S12 --.

Column 26, Line 46:
Please delete "(".

Column 27, Line 3-4:
Please add "measuring unit" to -- the contact pressure measuring unit Uijp --.

Column 29, Line 49:
Please change "$\tau$y" to -- $\tau x$ --.

Column 30, Line 56-57:
Please change "2" to -- 3 --.

Signed and Sealed this
Eighteenth Day of May, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,859,449 B2

Column 31, Line 4-5:
Please change "Uijτy" to -- Uijτx --.

Column 31, Line 41-42:
Please change "109" to -- 110 --.

Column 33, Line 54:
Please change "42R3" to -- 42-R3 --.

In the Claims

Claim 4, at Column 35, Line 17:
Please change "ingredient" to -- material --.

Claim 8, at Column 36, Line 61-65:
Please change "$\frac{V_p}{E} = \frac{R}{(R_0 + \Delta R_p)}$ (1)" to -- $\frac{V_p}{E} = \frac{R}{(R_0 + \Delta R_p)}$ (1) --.